United States Patent [19] [11] 3,992,437
Shaw et al. [45] Nov. 16, 1976

[54] POLYHYDROPHENANTHRENE DERIVATIVES

[75] Inventors: Philip E. Shaw, Winter Haven, Fla.; Sol J. Daum, Albany; Robert L. Clarke, Bethlehem, both of N.Y.

[73] Assignee: Sterling Drug Inc., New York, N.Y.

[22] Filed: Apr. 7, 1975

[21] Appl. No.: 565,957

Related U.S. Application Data

[60] Division of Ser. No. 393,623, Aug. 31, 1973, Pat. No. 3,922,312, which is a division of Ser. No. 269,402, July 6, 1972, Pat. No. 3,830,843, which is a division of Ser. No. 879,920, Nov. 25, 1969, Pat. No. 3,755,361, which is a continuation-in-part of Ser. No. 585,762, Oct. 11, 1966, Pat. No. 3,592,838.

[52] U.S. Cl. .................. 260/488 B; 260/293.56; 260/410; 260/468 H; 260/476 C; 260/482 C; 260/486 R; 260/586 E; 260/586 F
[51] Int. Cl.² .................. C07C 69/12; C07C 49/54

[58] Field of Search ............ 260/586 E, 488 B, 410, 260/468 H, 476 C, 486 R, 482 C, 293.56

[56] References Cited
UNITED STATES PATENTS
3,553,251   1/1971   Riehen et al. .................. 260/488 B

*Primary Examiner*—Gerald A. Schwartz
*Attorney, Agent, or Firm*—Thomas L. Johnson; B. Woodrow Wyatt

[57] ABSTRACT

Alkyl polyhydro-2-phenanthrylideneacetates are prepared by interacting the corresponding 2-oxopolyhydrophenanthrenes with a tri-lower-alkyl α-phosphono-lower-alkanoate. Said alkyl polyhydro-2-phenanthrylideneacetates are hydrolyzed to the free acid, and then reesterified via the acid chloride with a tertiaryamino-lower-alkanol to give basic esters having cardiotonic activity.

5 Claims, No Drawings

POLYHYDROPHENANTHRENE DERIVATIVES

This is a division of application Ser. No. 393,623, filed Aug. 31, 1973, now U.S. Pat. No. 3,922,312, which is in turn a division of our copending application Ser. No. 269,402, filed July 6, 1972, now U.S. Pat. No. 3,830,843, which is in turn a division of our copending application Ser. No. 879,920, filed Nov. 25, 1969, now U.S. Pat. No. 3,755,361, which is in turn a continuation-in-part of our prior copending application Ser. No. 585,762, filed Oct. 11, 1966, now U.S. Pat. 3,592,838.

This invention relates to tricyclic substituted acids and esters thereof, and in particular is concerned with polyhydro-2-phenantrylideneacetic acids and basic esters thereof, and with intermediates in the preparation thereof.

One aspect of the invention is concerned with compounds of the formula

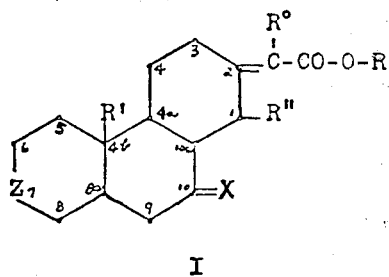

I wherein:
R is hydrogen, lower-alkyl or amino-lower-alkyl;
R' is hydrogen, lower-alkyl or hydroxy;
R'' and R° are hydrogen or lower-alkyl;
X is H$_2$, (H) (OH), (H)(O-acyl) or =O; and
Z is O=C, (HO)CH, (acyl-O)CH, CH$_2$, (lower-alkyl)-C(OH), (lower-alkoxy)CH, (halogen)CH, H$_2$NC(=NH)NHN=C, (O$_2$NO)CH, (C$_6$H$_5$CH$_2$S)$_2$C, (C$_6$H$_5$CH$_2$SO$_2$)$_2$C, [(lower-alkyl)$_2$N]CH, (piperidino)CH, (pyrrolidino)CH, (4-hydroxypiperidino)CH,

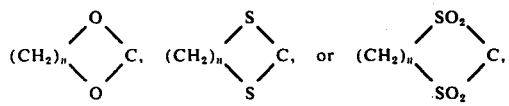

where
n is 2 or 3. Also included are compounds of formula I having a double bond in the 8,8a-position or the 8a,9-position; compounds of formula I wherein the exocyclic double bond is saturated; and compounds of formula I having two identical lower-alkyl groups in the 8-position.

The term "lower-alkyl" used above in defining the groups R, R'' and R° and certain subgroups under Z stands for alkyl groups having up to about six carbon atoms, including such groups as methyl, ethyl, propyl, isopropyl, butyl, hexyl, and the like.

When R in Formula I stands for an amino-lower-alkyl group, it represents a lower-alkyl group substituted by a basic amino group. The exact nature of the basic amino moiety is not critical, although it is preferred that it have a molecular weight less than about 200. A particularly preferred type of amino-lower alkyl group has the structure —Y—N=B wherein Y is lower-alkylene of 2–5 carbon atoms and N=B is unsubstituted amino, lower-alkylamino, di-lower-alkylamino, polymethylenimino of 5–7 ring carbons and lower-alkylated derivatives thereof, 4-morpholinyl and lower-alkylated derivatives thereof, or 1-piperazinyl and lower-alkylated derivatives thereof. The term "lower-alkyl" as used in defining portions of the amino moiety N=B stands for alkyl groups having up to about six carbon atoms.

When Z is formula I above stands for (acyl—O)CH, or X stands for (H) (O—acyl), the acyl groups are carboxylic acyl groups having from one to twelve carbon atoms and molecular weights less than about 250. Representative of the lower-carboxylic acyl radicals which can be present are lower-alkanoyl, e.g., acetyl, propionyl, isobutyryl, caproyl, heptanoyl, octanoyl, dodecanoyl, trimethylacetyl, and the like; cycloalkyl-lower-alkanoyl wherein cycloalkyl has 5–6 ring members, e.g., β-cyclopentylpropionyl, β-cyclohexylpropionyl, and the like; benzoyl; phenyl-lower-alkanoyl or -alkenoyl, e.g., phenylacetyl, β-phenylpropionyl, cinnamoyl, and the like; phenoxy-lower-alkanoyl, e.g., p-chlorophenoxyacetyl; carbamyl, including unsubstituted carbamyl, N-lower-alkylcarbamyl, N-phenyl-carbamyl and N,N-di-lower-alkylcarbamyl; and pyridylcarbonyl, e.g., nicotinoyl and isonicotinoyl. In acyl radicals containing a phenyl group, the benzene ring thereof can be unsubstituted or substituted by any number and kind of substituents inert under the reaction conditions used, including lower-alkyl, for example p-tolyl; lower-alkoxy, for example 3,4-dimethoxyphenyl; halogen (including fluorine, chlorine, bromine and iodine), for example 2-bromophenyl; and nitro, for example p-nitrophenyl. The lower-alkyl and lower-alkoxy groups preferably have from one to four carbon atoms.

The invention is not limited to any particular stereochemical configuration of the compounds of formula I, although a preferred configuration of the ring system is trans-anti-trans (4aα,4bβ,8aα,10aβ), such compounds being derived from readily available starting materials.

A further aspect of the invention is concerned with compounds of the formula

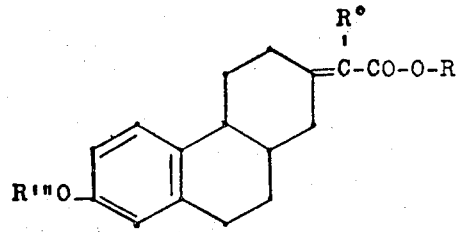

II wherein:
R is hydrogen, lower-alkyl or amino-lower-alkyl;
R° is hydrogen or lower-alkyl; and
R''' is hydrogen, lower-alkyl or carboxylic acyl of 1–12 carbon atoms.

The terms lower-alkyl, amino-lower-alkyl and acyl have the meanings given above. The invention is not limited to any particular stereochemical configuration of the compounds of formula II, although a preferred configuration is 4aα,10aβ, such compounds being derived from readily available starting materials.

The compounds of formulas I and II wherein R is lower-alkyl are prepared from compounds of formulas III and IV, respectively, including compounds of formula III having a double bond in the 8,8a-position, Z being C=O, and compounds of formula III having two identical lower-alkyl groups in the 8-position and a double bond in the 8a,9-position, Z being C=O:

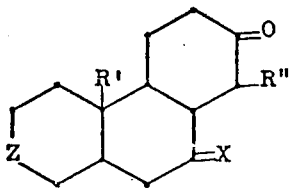

III

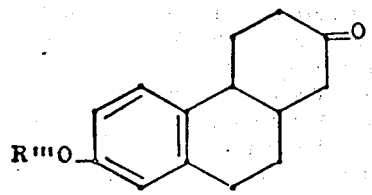

IV by reacting compounds of formulas III and IV with a tri-lower-alkyl α-phosphono-lower-alkanoate of the formula

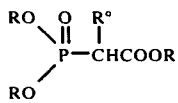

in the presence of a basic compound capable of acting as a proton acceptor. Examples of such basic compounds are alkali metal alkoxides, amides or hydrides, e.g., sodium ethoxide, sodium amide or sodium hydride, and the reaction is preferably carried out in non-aqueous medium at room temperature. The compounds of formula I where X is O can be prepared in this manner because the 10-oxo group is relatively unreactive compared to the 2-oxo group.

It is preferred to employ compounds of formula III wherein Z is (HO)CH, (acyl-O)CH, CH₂, (lower-alkyl)C(OH), (lower-alkoxy)CH, (halogen)CH, (C₆H₅CH₂S)₂C,

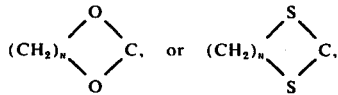

in the reaction with a tri-lower-alkyl α-phosphono-lower-alkanoate; however, Z can also be O=C if a double bond is present at the 8,8a-position, or two identical lower-alkyl groups are in the 8-position. The compounds of formula I wherein Z is O=C, (acyl-O)CH, H₂NC(=NH)NHN=C, (O₂NO)CH, [(lower-alkyl)₂N]CH, (piperidino)CH, (4-hydroxypiperidino)CH, or (pyrrolidino)CH can readily be prepared from the compounds of formula I wherein Z is (HO)CH or O=C by conventional means as illustrated in the examples below.

The reaction of compounds of formulas III and IV with a tri-lower-alkyl α-phosphono-lower-alkanoate gives a mixture of geometric isomers (cis and trans) involving the groups about the exocyclic double bond. Although in many instances it is possible to separate the isomers by physical means, it is not essential to the present invention that the isomers be separated because there is little difference in the physiological properties of the isomers.

The compounds of formulas I and II wherein R is hydrogen are prepared by alkaline hydrolysis of the compounds of formulas I and II wherein R is lower-alkyl.

The compounds of formulas I and II wherein R is amino-lower-alkyl are prepared by esterification of the compounds of formulas I and II wherein R is hydrogen by employing the appropriate amino-lower-alkanol or amino-lower-alkyl halide. A preferred method comprises reacting the acid halide of a free acid of formulas I or II with a tertiary-amino-lower-alkanol, although an alternative procedure involves reacting an alkali metal salt (e.g. sodium salt) of the acid with an amino-lower-alkyl halide (e.g., chloride or bromide). Surprisingly, the acid halide process can be used even in the presence of a free hydroxy group [Z=(HO)CH]. It appears that if reaction does occur at the hydroxy group during acid halide formation, the hydroxy group is regenerated during the preparation of the basic ester.

The products of formulas I and II are obtained in the form of racemic mixtures of optically active d- and l-forms. If desired, the latter can be separated by conventional resolution procedures, for example, by treatment of the compounds where R is hydrogen with dehydroabietylamine.

The intermediates of formula IV can be prepared as illustrated in the following flow sheet.

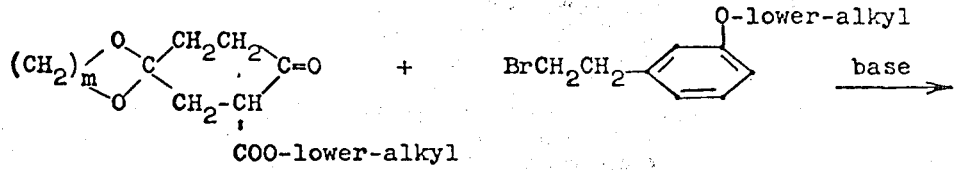

[contd.]

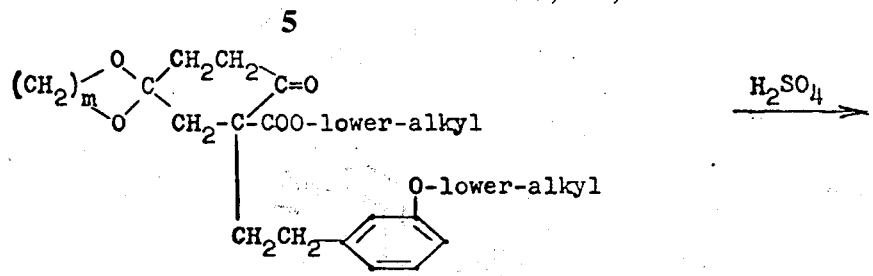
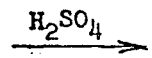
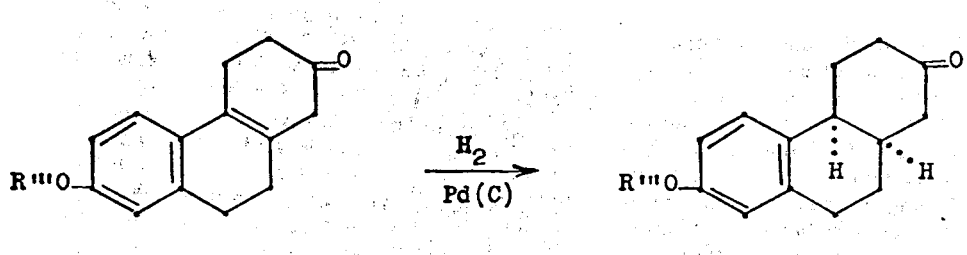
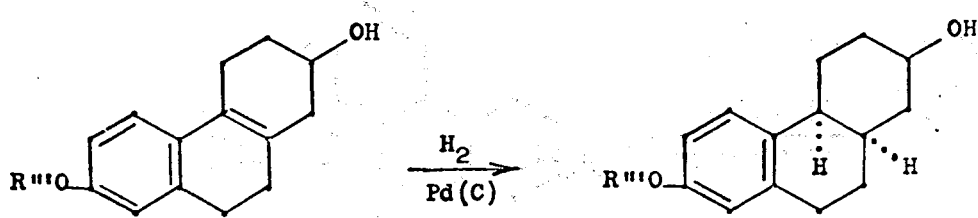
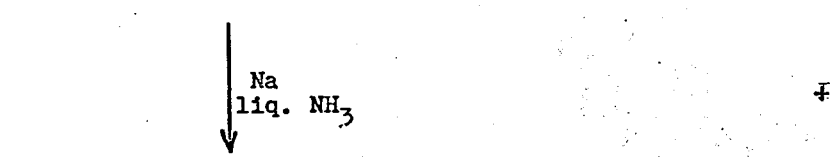
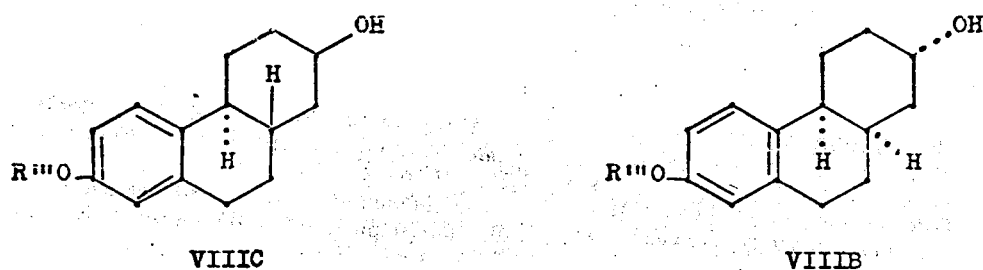

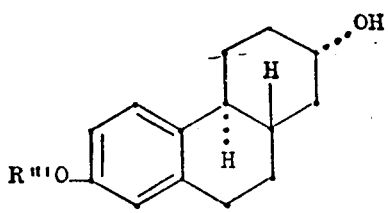

VIIID

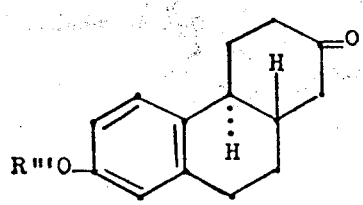

IVB

A 2-carbo-lower-alkoxycyclohexane-1,4-dione 4-ketal (m = 2 or 3) is aralkylated with a m-lower-alkoxyphenylethyl bromide, and the resulting product V is cyclized with acid to yield 3,4,9,10-tetrahydro-7-lower-alkoxy-2(1H)-phenanthrone (VI). Catalytic hydrogenation of VI with palladium-on-carbon gives a compound of formula IV having the 4aα,10aα-configuration (IVA). Sodium borohydride reduction of VI gives 1,2,3,4,9,10-hexahydro-7-methoxy-2-phenanthrol (VII). Sodium-liquid ammonia reduction of the latter provides a mixture of 1,2,3,4,4aα,9,10,10aβ-octahydro-7-lower-alkoxy-2β- and 2α-phenanthrol (VIIIC and VIIID), which can be oxidized with chromic oxide to give a compound of formula IV having the 4aα,10aβ-configuration (IVB). Sodium borohydride reduction of IVA gives a mixture of 1,2,3,4,4aα,9,10,10aα-octahydro-7-lower-alkoxy-2β- and 2α-phenanthrol (VIIIA and VIIIB).

The compounds of formula III wherein R' and R'' are hydrogen, X is H₂ and Z is (HO)CH are prepared by reduction of the octahydrophenanthrenes of formulas VIIIA-D, as follows:

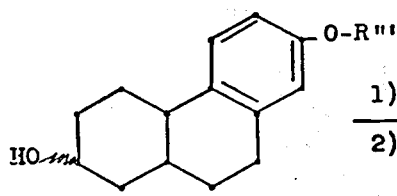

VIII

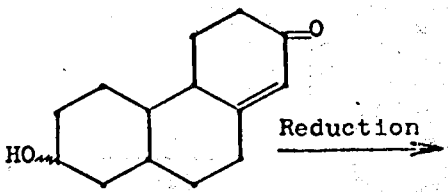

IX

A compound of formula VIII is first reduced with lithium and liquid ammonia in the presence of alcohol (Birch reduction) followed by hydrolysis to give a 4,4a,4b,5,6,7,8,8a,9,10-decahydro-7-hydroxy-2(3H)-phenanthrone (IX), which can then be reduced further either catalytically or by alkali metal-ammonia recuction to give 3,4,4a,4b,5,6,7,8,9,10,10a-dodecahydro-7-hydroxy-2(1H)-phenanthrone (X) (III; Z is (HO)CH, R' and R'' = H, X = H₂). The stereochemistry of the ring system and the 7-hydroxy group is dependent upon the particular VIII isomer used and the nature of the reduction of IX, as will be apparent from the specific examples below. The function groups of X can also be altered by conventional means as will be illustrated by the examples below.

The compounds of formula III wherein R' is methyl can be prepared from the compound:

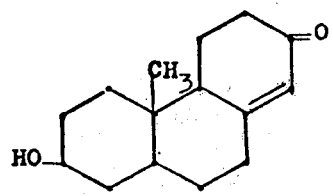

XI

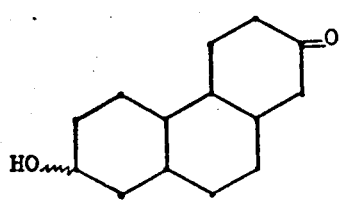

X

Reduction of the double bond of XI affords a compound of formula III wherein Z is (HO)CH, R' is CH₃, R'' is H and X is H₂.

The compounds of formula III wherein R'' is lower-alkyl are prepared from compounds of the formula

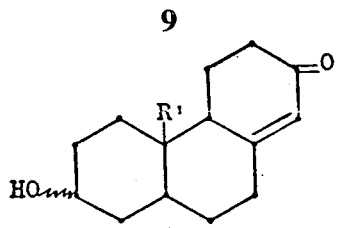

IX (R' = H)

XI (R' = CH₃)

by reductive alkylation with lithium in liquid ammonia and a lower-alkyl halide.

The compounds of formula III wherein R' is OH or X is O can be prepared by microbiological oxidation of compound IX above. When IX is incubated with a culture medium of an organism of the genus *Cunninghamella* there is obtained a mixture of the hydroxylated products:

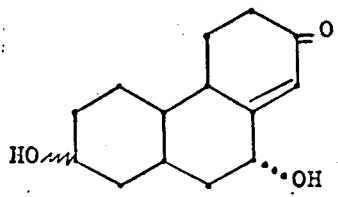 and 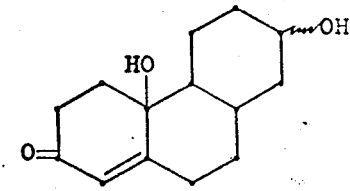

XII           XIII

Treatment of XII with sulfuric acid in acetic acid converts it by rearrangement to a compound of formula III where Z is (CH₃COO)CH, R' is H, R'' is H and X is =O. Oxidation of XIII with chromic oxide converts it to a compound of formula III wherein Z is O=C, R' is OH, R'' is H, X is H₂, and there is a double bond in the 8,8a -position.

The compounds of formula III wherein there are two lower-alkyl groups in the 8-position and a double bond in the 8a,9-position, Z being O=C, are prepared as follows:

X is O, Z is O=C, 8,8-di-lower-alkyl, $\Delta^{8a,9}$). Alternatively, the compounds XV or XVI can be oxidized with tertiary-butyl peracetate in the presence of cuprous chloride to introduce an acyloxy group into the 10-position. Hydrolysis and oxidation of the latter than gives the triketone XVII.

Further starting materials for the preparation of compounds of formula I having two identical lower-alkyl groups are of the formula

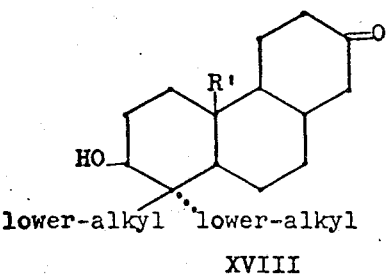

lower-alkyl  lower-alkyl

XVIII where R' is hydrogen or lower-alkyl. The compounds of formula XVIII can be prepared from compounds of formula XVI by forming the mono-ethylene glycol ketal of the 2oxo group, reducing the 8-oxo group with lithium aluminum hydride to an 8β-hydroxy group, reducing the 8a,9-double bond with hydrogen in the presence of palladium-on-carbon, and finally cleaving the 2-ketal group.

The compounds of formula I where the exocyclic double bond is saturated can be prepared by hydrogenation (palladium-on-carbon) of the unsaturated ana-

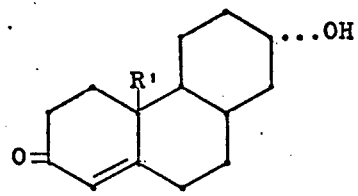 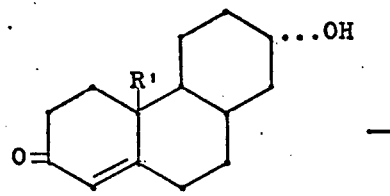

XIV           XV

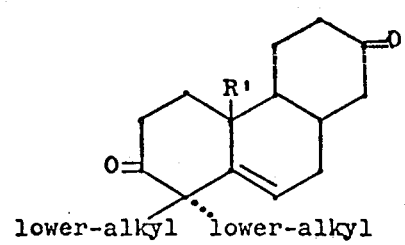 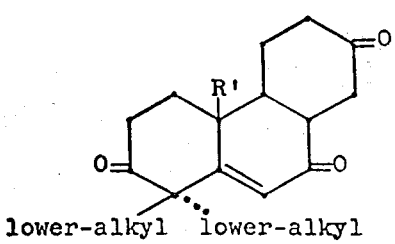

lower-alkyl  lower-alkyl       lower-alkyl  lower-alkyl

XVI           XVII

Alkylation of XIV (R is hydrogen or lower-alkyl) with a lower-alkyl halide in the presence of potassium tertiary-butoxide gives a hydroxy ketone of formula XV. The latter can be oxidized with chromic oxide to the diketone XVI. The 10-oxo group can then be introduced by the action of tertiary-butyl chromate to give the triketone XVII (III; R' is H or lower-alkyl, R'' is H, logs where R is lower-alkyl.

The structures of the compounds of the invention were established by the modes of synthesis, by elementary analysis, by interpretation of their infrared, ultraviolet and NMR spectra, and by their behavior and in thin layer chromatography (TLC) and gas-liquid phase chromatography (glpc).

The compounds of formulas I and II wherein R is amino-lower-alkyl are basic in nature and form acid-addition salts with moderate to strong inorganic or organic acids. For pharmacological purposes it is preferred to use water-soluble, pharmaceutically acceptable acid-addition salts, although all acid-addition salts are useful as characterizing derivatives of and as intermediates in the purification of the free bases.

Pharmacological evaluation of the basic ester compounds of the invention has shown that they possess cardiotonic activity similar to that shown by the alkaloid cassaine and are thus useful in increasing the ventricular contractile force of the mammalian heart. The compounds are prepared for use in the form of a sterile aqueous solution of a water-soluble, pharmaceutically acceptable acid-addition salt. The amidino-hydrazone derivatives of the intermediate tricyclic ketones also have similar cardiotonic activity.

Chemotherapeutic evaluation has shown that the compounds of formula I wherein R is hydrogen possess bacteriostatic activity.

The following examples will further illustrate the invention without the latter being limited thereby.

EXAMPLE 1

2-Carbomethoxy-2-(m-methoxyphenethyl)-cyclohexane-1,4-dione 4-ethylene ketal [V; R''' is $CH_3$].

A solution of 5.33 g. (0.047 mole) of potassium t-butoxide in 100 ml. of t-butanol was stirred while 10.0 g. (0.047 mole) of 2-carbomethoxycyclohexane-1,4-dione 4-ethylene ketal in 150 ml. of t-butanol was added. An additional 100 ml. of t-butanol was added, followed by 10 g. (0.047 mole) of m-methoxyphenethyl bromide. The suspension was refluxed and stirred mechanically for 72 hours. At this point the reaction mixture was slightly alkaline to pH paper. The reaction mixture was cooled and added to ice water. Ether was added followed by dilute hydrochloric acid. The layers were separated, and the ether layer was washed with a saturated sodium bicarbonate solution. The ether was extracted twice with 200-ml. portions of 5% aqueous potassium hydroxide. The aqueous alkaline solution on acidification with hydrochloric acid yielded 1.45 g. of starting 2-carbomethoxycyclohexane-1,4-dione 4-ethylene ketal which was identified by its melting point. The ether solution from which the starting material had been removed was then washed with ice cold dilute hydrochloric acid, saturated sodium bicarbonate solution and saturated sodium chloride. After drying the ether solution ($Na_2SO_4$), the solvent was removed to leave a yellow viscous oil. This residue was distilled and the fraction that boiled at 190°–205°C. (0.08–0.15 mm.) was collected to give 10.1 g. of 2-carbomethoxy-2-(m-methoxyphenethyl)-cyclohexane-1,4-dione 4-ethylene ketal. A redistilled sample boiled at 195°–196° C. (0.18–0.20 mm.); $_D^{25}$ = 1.5267.

EXAMPLE 2

3,4,9,10-Tetrahydro-7-methoxy-2(1H)-phenanthrone

[VI; R''' is $CH_3$].

Sulfuric acid (1 liter 11N) was added all at once to a solution containing 115.4 g. (0.33 mole) of 2-carbomethoxy-2-(m-methoxyphenethyl)-cyclohexane-1,4-dione 4-ethylene ketal (Example 1) in 1 liter of dioxane. The reaction mixture was stirred at 100° C. in a nitrogen atmosphere for 4½ hours. The cooled solution was poured into ice and enough water was added to bring the total volume to 3 liters. The aqueous mixture was extracted with ether several times. The combined ether layers were washed with 10% sodium carbonate and finally with saturated sodium chloride solution. The ether solution was dried ($Na_2SO_4$) and evaporated by warming in vacuo to afford 73.9 g. of a red oil. This material was chromatographed on 2 kg. of silica gel. Elution with 4 liters of ether-pentane (1:9) and 20 liters of ether-pentane (1:3) removed less polar material. Continued elution with 5.5 liters of ether-pentane (1:3) afforded 18.2 g. of an oil which crystallized from ether containing hexane to give 16.5 g. of 3,4,9,10-tetrahydro-7-methoxy-2(1H)-phenanthrone, m.p. 75°–77° C. Further elution (5 liters) gave an additional 17.8 g. of the compound.

EXAMPLE 3

1,2,3,4,9,10-Hexahydro-7-methoxy-2-phenanthrol

[VIII; R''' is $CH_3$].

A solution of 36.7 g. (0.16 mole) of 3,4,9,10-tetrahydro-7-methoxy-2(1H)-phenanthrone (Example 2) in 1500 ml. of 95% ethanol was treated with 19 g. of sodium borohydride in 150 ml. of water. After 3 hours at room temperature, acetone was added to the reaction mixture to decompose the excess borohydride. The volume was reduced to about 400 ml. by warming in vacuo. Water and ether were added and the layers were separated. The ether was washed with saturated sodium chloride solution. The aqueous layers were washed again with fresh ether and the organic layers were then combined. The ether solution was dried ($Na_2SO_4$) and the solvent was removed leaving behind an oily residue (36.1 g.). Crystallization from ether containing hexane gave 20.3 g. of 1,2,3,4,9,10-hexahydro-7-methoxy-2-phenanthrol, m.p. 93°–94° C. Further concentration of the mother liquor afforded another 9.3 g. of the compound, m.p. 90°–92° C.

EXAMPLE 4

3,4,4aα,9,10,10aα-Hexahydro-7-methoxy-2(1H)-phenanthrone

[IVA; R''' is $CH_3$].

A solution of 1 g. (4.4 mmoles) of 3,4,9,10-tetrahydro-7-methoxy-2(1H)-phenanthrone (Example 2) in 300 ml. of ethyl acetate was hydrogenated at a pressure of 3.86 kg./cm² and room temperature in the presence of 100 mg. of 10% palladium-on-carbon. After 1 hour the hydrogenation was complete and the catalyst was removed by filtration. The solvent was removed by warming in vacuo and the residue was crystallized from ether containing hexane to yield 900 mg. of 3,4,4aα,9,10,10aα-hexahydro-7-methoxy-2(1H)-phenanthrone, m.p. 92°–93° C. and a second crop (100 mg.), m.p. 89°–91° C.

EXAMPLE 5

1,2,3,4,4aα-Octahydro-7-methoxy-2β-phenanthrol and -2α-phenanthrol

[VIIIA and B; R''' is $CH_3$].
Method 1.

A solution of 15 g. (0.066 mole) of 1,2,3,4,9,10-hexahydro-7-methoxy-2-phenanthrol (Example 3) in 300 ml. of ethyl acetate was hydrogenated at a pressure of 3.86 kg./cm² and room temperature in the presence of 1.5 g. of 10% palladium-on-carbon. After 45 minutes the hydrogenation was complete and the catalyst was removed by filtration. The filtrate was combined with the filtrate of an identical experiment. The solvent was removed by warming in vacuo to leave 31.5 g. of an oily residue which crystallized from ether containing hexane. Recrystallization of this material from ether containing hexane afforded 13.6 g. of solid, m.p. 80°–83° C.

The mother liquor was chromatographed on 1.5 kg. of silica gel. Elution with 13 liters of ether-pentane (1:1) removed some less polar material. Continued elution with 5.5 liters of solvent of the same concentration afforded 6 g. of material which, on crystallization from ether containing hexane, yielded 4.83 g. of solid, m.p. 84°–87° C. and 0.4 g. of solid, m.p. 81°–85° C. Combination with the original solid obtained by direct crystallization and recrystallization from ether containing hexane afforded 16.1 g. of 1,2,3,4,4aα,9,10,10aα-octahydro-7-methoxy-2β-phenanthrol (VIIIA), m.p. 84°–88° C. This compound apparently shows polymorphism. Recrystallization from ether containing hexane gave material melting at 77°–82° C.

Further elution in the above described chromatography, with 2.5 liters of ether-pentane (1:1) gave 4.2 g. of a mixture of two compounds. Finally, elution with another 4 liters of the same solvent mixture gave an oily residue which crystallized from ether containing hexane and afforded 5.3 g. of 1,2,3,4,4aα,9,10,-10aα-octahydro-7-methoxy-2α-phenanthrol (VIIIB), m.p. 67°–70° C. Recrystallization from ether containing hexane gave 5 g., m.p. 89°–90.5° C.

(Method 2)

A solution of 580 mg. (2.5 mmoles) of 3,4,4aα,9,10,-10aα-hexahydro-7-methoxy-2(1H)-phenanthrone (Example 4) in 25 ml. of absolute ethanol was treated with 240 mg. of sodium borohydride in 2.5 ml. of water. The reaction mixture was kept at room temperature overnight and the excess borohydride was decomposed by adding acetone followed by water. The reaction mixture was washed with ether and the ether was washed with saturated sodium chloride solution. The ether was dried ($Na_2SO_4$) and evaporated to leave 500 mg. of oily residue.

The oily residue was chromatographed on silica gel-coated plates which were developed with ether-pentane (3:1). About 170 mg. of residue was put on each of 3 plates (20 × 40 cm) carrying a 1-mm. coating of silica gel. The major band from the plates (less polar) afforded 310 mg. (54%) of 1,2,3,4,4aα,9,10,10aα-octahydro-7-methoxy-2β-phenanthrol (VIIIA), which was identified by melting point, infrared spectrum and TLC analysis. The more polar band afforded 110 mg. (19%) of 1,2,3,4,4aα, 9,10,10aα-octahydro-7-methoxy-2α-phenanthrol (VIIIB) which is identified by melting point, infrared spectrum and TLC analysis.

EXAMPLE 6

1,2,3,4,4aα,9,10,10aβ-Octahydro-7-methoxy-2β-phenanthrol and -2α-phenanthrol

[VIIIC and D; R''' is $CH_3$].

Sodium (3.15 g., 0.137 mole) was dissolved in 1 liter of liquid ammonia. A solution of 15 g. (0.066 mole) of 1,2,3,4,9,10-hexahydro-7-methoxy-2-phenanthrol (Example 3) in 100 ml. of tetrahydrofuran and 25 ml. of aniline was added over a 20 minute period to the ammonia solution which was being stirred. At the end of the addition 14 g. (0.26 mole) of ammonium chloride was added portion-wise during 5 minutes to discharge the blue color. The ammonia was evaporated and water and ether were added to the residue. The aqueous layer was separated and extracted twice with ether. The combined ether layers were washed 3 times with water, twice with 3N hydrochloric acid, three times with saturated sodium chloride solution, dried ($Na_2SO_4$), and the solvent was removed to leave an amber colored residue. After crystallization and several recrystallizations from ether containing hexane, 4.7 g. of 1,2,3,4,4aα,9,10,10aβ-octahydro-7-methoxy-2α-phenanthrol (VIIIC), m.p. 98°–99° C. was obtained.

The combined mother liquors were chromatographed on 5 kg. of silica gel. Preliminary elution with ether-pentane (1:1) separated some less polar oils which were discarded. Continued elution with ether-pentane (1.1:1) afforded first 15 g. of crude 1,2,3,4,4aα,9,10,10aβ-octahydro-7-methoxy-2β-phenanthrol. Continued elution with the same solvent system next afforded 12 g. of crude 1,2,3,4,4aα, 9,10,10aα-octahydro-7-methoxy-2β-phenanthrol (VIIIA). Further elution with ether-pentane (1.5:1) finally gave 53 g. of an oil which yielded 13 g. more of 1,2,3,4,4aα, 9,10,10aβ-octahydro-7-methoxy-2α-phenanthrol (VIIID), m.p. 98°–100° C.

Recrystallization of the crude 1,2,3,4,4aα, 9,10,10aβ-octahydro-7-methoxy-2β-phenanthrol from ether afforded 13.75 g. of this product.

A similar chromatographic separation afforded 1,2,3,4,9,10-hexahydro-7-hydroxy-2-phenanthrol [VII; R''' is H], m.p. 196.5°–198° C. (10%) when 100% ether was put through the column.

EXAMPLE 7

3,4,4aα,9,10,10aβ-Hexahydro-7-methoxy-2(1H)-phenanthrone

[IVB; R''' is $CH_3$[

A solution of 25 g. (0.11 mole) of 1,2,3,4,4aα, 9,10, 10aβ-octahydro-7-methoxy-2α-phenanthrol in 500 ml. of pyridine was added to a suspension of 25 g. of chromium trioxide (0.25 mole) in 500 ml. of pyridine. After standing at room temperature for 68 hours, the reaction mixture was added to 1.5 liters of ethyl acetate. The chromium salts were removed by passing the suspension through infusorial earth. The solvent was removed by heating in vacuo. Ether was added to the viscous residue and the mixture was filtered again. Evaporation of the ether afforded 20 g. of viscous oil. Crystallization from cyclohexane containing ether afforded 6 g. of 3,4,4aα, 9,10,10aβ-hexahydro-7-methoxy-2(1H)-phenanthrone, m.p. 62°–63° C. Concentration of the mother liquor afforded another 4 g., m.p. 59°–62° C. Chromatography of the mother liquors on sillica gel and elution with ether-pentane (1:3) afforded an additional 6.14 g. of 3,4,4aα, 9,10,10aβ-hexahydro-7-methoxy-2(1H)-phenanthrone, m.p. 64.5°–66° C. when recrystallized from ether-hexane.

EXAMPLE 8

4,4aα,4bβ,5,6,7,8,8aβ,9,10,-Decahydro-7α-hydroxy-2(3H)-phenanthrone [IX; 7α,4aα,4bβ,8aβ-configuration[.

A solution of 11 g. (0.05 mole) of 1,2,3,4,4aα, 9,10,10aα-octahydro-7-methoxy-2β-phenanthrol (VIIIA, Example 5) in 200 ml. of tetrahydrofuran and 200 ml. of t-butyl alcohol was added to 400 ml. of ammonia. Lithium (5.5 g., 0.79 mole) was added to the stirred solution over a 2 hour period. The reaction mixture, which never became blue but developed a bronze-colored layer, was stirred for an additional four hours. Methanol (60 ml.) was added and the ammonia was evaporated. Water and ether were added, the mixture shaken and the layers separated. The ether layer was washed twice with saturated sodium chloride solution. The aqueous layers were washed with a fresh portion of ether and the ether layers were combined, dried (Na$_2$SO$_4$) and concentrated by warming in vacuo. The syrupy residue was dissolved in 150 ml. of dioxane. The dioxane solution was treated with 75 ml. of 2N hydrochloric acid and heated in a nitrogen atmosphere on a steam bath for 30 minutes. Saturated sodium chloride solution and ether were added to the cooled reaction mixture, the mixture shaken and the layers separated. The ether was washed again with saturated sodium chloride solution. The aqueous layers were washed again with a fresh portion of ether. The combined ether layers were dried (Na$_2$SO$_4$) and evaporated by warming in vacuo to leave 11 g. of an oily residue. Crystallization from acetone afforded 5.36 g. of 4,4aα,4bβ,5,6,7,8,8aβ,9,10-decahydro-7α-hydroxy-2(3H)-phenanthrone, m.p. 148°–151° C., and a crop of 0.4 g., m.p. 144°–147° C. Recrystallization from acetone provided a sample with m.p. 150°–152° C.

EXAMPLE 9

4,4aα,4bβ, 5,6,7,8,8aα, 9,10-Decahydro-7β-hydroxy-2(3H)-phenanthrone [IX; 7β,4aα,4bβ,8aα-configuration].

A solution of 18.33 g. (0.08 mole) of 1,2,3,4,4aα,9,-10,10aβ-octahydro-7-methoxy-2α-phenanthrol (VIIIB, Example 5) in 186 ml. of tetrahydrofuran was added to 300 ml. of ammonia. Lithium wire (5.5 g., 0.8 mole) was added in 30 minutes with stirring. After an additional 25 minutes a mixture of 60 ml. of absolute ethanol and 60 ml. of ether (anhydrous) was added to discharge the blue color. The solution was evaporated to half the volume. Ether and water were added, the mixture shaken and the layers separated. The ether was washed with saturated sodium chloride solution and the aqueous layers were washed with a fresh portion of ether. The combined ether layers were dried (Na$_2$SO$_4$) and the ether was removed by warming in vacuo. The remaining residue was taken up in 300 ml. of dioxane and 150 ml. of 2N hydrochloric acid. The solution was heated in a nitrogen atmosphere for 30 minutes on a steam bath. Saturated sodium chloride solution and ether were added to the cooled reaction mixture and the layers were separated. The ether was washed twice with saturated sodium chloride solution. The aqueous layers were washed with a fresh portion of ether. The combined ether was dried (Na$_2$SO$_4$) and the solvent was removed while warming in vacuo, leaving 18 g. of an oily residue that crystallized from ether. Several recrystallizations from ether afforded 9.82 g. of 4,4aα,4bβ,5,6,7,8,8aα,9,10-decahydro-7β-hydroxy-2(3H)phenanthrone, m.p. 141°–143° C., when recrystallized from acetone.

EXAMPLE 10

4,4aα,4bβ,5,6,7,8,8aα,9,10-Decahydro-7α-hydroxy-2(3H)-phenanthrone [IX; 7α,4aα,4bβ,8aα-configuration].

1,2,3,4,4aα,9,10,10aβ-Octahydro-7-methoxy-2β-phenanthrol (VIIIC, Example 6) (15.5 g., 0.024 mole), by the procedure of Example 9, afforded 2.8 g. of 4,4aα,4bβ,5,6,7,8,8aα,-9,10-decahydro-7α-hydroxy-2(3H)-phenanthrone, m.p. 126.5°–128.5° C., and a second crop of 0.6 g., m.p. 123.5°–127° C. (yield 64%), when recrystallized from acetone.

EXAMPLE 11 a. 1,2,3,4,4aα,4bβ,5,6,7,8,8aα,9,10,10aα-Tetradecahydrophenanthrene-2β,7β-diol 7-acetate.

A solution of 6.95 g. (0.031 mole) of 4,4aα,4bβ,5,6,7,8,8aβ,9,10-decahydro-7α-hydroxy-2(3H)-phenanthrone (Example 8) in 250 ml. of tetrahydrofuran and 250 ml. of ether was treated with 20 ml. of dihydropyran and 200 mg. of p-toluenesulfonic acid, and the solution was left at room temperature overnight. Solid sodium carbonate was added to neutralize the acid and the solution was passed through a filter. Pyridine (2 ml.) was added and the volume of the solution was reduced to about 30 ml. by heating the mixture in vacuo. Tetrahydrofuran (30 ml.) and absolute ethanol (60 ml.) were added to the residue and the resulting solution was added to 500 ml. of liquid ammonia. A total of 7 g. (1 mole) of lithium wire was added to the stirred ammoniacal solution over a 45 minute period. The solution remained blue for about one hour after addition of the lithium and 30 ml. more of absolute ethanol was added to discharge the color. The volume was reduced to one-third. Ether was added and the solution was heated under reflux conditions to remove more of the ammonia. Water was carefully added, followed by more ether. The layers were separated and the ether was washed with saturated sodium chloride solution. The aqueous layers were washed with a fresh portion of ether and the combined ether layers were dried (Na$_2$SO$_4$). The solvent was removed in vacuo to afford 1,2,3,4,4aα,4bβ,5,6,7,8,8aα,9,10,-10aα-tetradecahydrophenanthrene-2β,7β-diol 2-dihydropyranyl ether. Pyridine (30 ml.) and acetic anhydride (15 ml.) were added to the residue. The next morning the excess reagents were removed by warming in vacuo. The residue was dissolved in 150 ml. of methanol and 150 ml. of 2N hydrochloric acid. At the end of 45 minutes, ether was added and the layers were separated. The ether was washed twice with saturated sodium chloride solution. The aqueous layers were washed with a fresh portion of ether and the combined ether layers were dried (Na$_2$SO$_4$). The solvent was removed by warming in vacuo and the residue was chromatographed on 250 g. of silica gel. The fractions eluted with methylene dichloride-ether-pentane (1:2:2), afforded 2.63 g. of 1,2,3,4,4aα,4bβ,5,6,7,8-,8aα,9,10,10aα-tetradecahydrophenanthrene-2β,7β-diol 7-acetate, m.p. 166.5°–167° C. when recrystallized from ether.

b. 1,2,3,4,4aα,4bβ,5,6,7,8,8aα,9,10,10aα-Tetradecahydrophenanthrene-2β,7β-diol.

A solution containing 150 mg. (0.6 mmoles) of 1,2,3,4,4aα,4bβ,5,6,7,8,8aα,9,10,10aα-tetradecahydrophenanthrene-2β,7β-diol 7-acetate in 15 ml. of 5% methanolic potassium hydroxide containing 5% water was boiled under reflux for 30 minutes. Water and ether were added, the mixture shaken and the layers separated. The aqueous layer was washed with a fresh portion of ether and the combined ether layers were washed with saturated sodium chloride, dried (Na$_2$SO$_4$) and concentrated in vacuo. The residue crystallized from ether containing hexane and gave 90 mg. (68%) of 1,2,3,4,4aα,4bβ,5,6,7,8,8aα,9,10,10aα-tetradecahydrophenanthrene-2β,7β-diol, m.p. 152.5°–153.5° C. when recrystallized from acetone containing hexane.

EXAMPLE 12

3,4,4aα,4bβ,5,6,7,8,8aα,9,10,10aα-Dodecahydro-7β-hydroxy-2(1H)-phenanthrone

[X; 7β,4aα,4bβ,8aα,10aα-configuration].

A pyridine solution (30 ml.) of 1,2,3,4,4aα,4bβ,5,6,7,8,8aα,9,10,10aα-tetradecahydrophenanthrene-2β,7β-diol 7-acetate (Example 11a) (2.4 g., 0.01 mole) was added to 30 ml. of pyridine containing 2.4 g. of chromium trioxide. After standing for 24 hours at room temperature the reaction mixture was added to 500 ml. of ethyl acetate and then filtered. The solvent was removed in vacuo and 150 ml. of ether was added to the residue. More salts were filtered away and the ether was evaporated. The residue containing 3,4,4aα,4bβ,5,6,7,8,8aα,9,10,10aα-dodecahydro-7β-hydroxy-2(1H)-phenanthrone 7-acetate was dissolved in 80 ml. of 5% methanolic potassium hydroxide containing 5% water and the solution was boiled under reflux for 45 minutes. Part of the methanol was removed by warming in vacuo. Ether and saturated sodium chloride were added. The mixture was shaken, the layers were separated and the ether was washed with saturated sodium chloride solution. The aqueous layers were washed again with a fresh portion of ether and the combined ether layers were dried (Na$_2$SO$_4$) and evaporated. Crystallization of the residue from ether afforded 1.64 g. of 3,4,4aα,4bβ,5,6,7,8-,8aα,9,10,10aα-dodecahydro-7β-hydroxy-2(1H)-phenanthrone, m.p. 116°–117.5° C. when recrystallized from ether.

EXAMPLE 13

3,4,4aα,4bβ,5,6,7,8,8aα,9,10,10aβ-Dodecahydro-7β-hydroxy-2(1H)-phenanthrone

[X; 7β,4aα,4bβ,8aα,10aβ-configuration].

A solution of 10.75 g. (0.049 mole) of 4,4aα,4bβ,5,6,7,8,8aα,9,10-decahydro-7β-hydroxy-2(3H)-phenanthrone (Example 9) in 225 ml. of tetrahydrofuran and 110 ml. of ether was added in a steady stream to a stirred solution of liquid ammonia (1.1 liter) containing 1.37 g. (0.19 mole) of lithium wire. The dropping funnel used for the addition was rinsed with another 55 ml. of tetrahydrofuran. Ammonium chloride (10 g., 0.19 mole) was added as quickly as possible with controlled boiling. The solvent was evaporated to half the volume. Water (300 ml.) and ether (300 ml.) were added. The ether was boiled under reflux to remove more of the ammonia. More ether and water were added and the layers were separated. The ether layer was washed with saturated sodium chloride and was then dried (Na$_2$SO$_4$). Evaporation of the ether left an oily residue of 11.6 g. The residue was chromatographed on 300 g. of silica gel. Elution with methylene dichloride-ether-pentane (2:5:3) afforded 7.9 g. of 3,4,4aα,4bβ,5,6,7,8,8aα,9,10,10aβ-dodecahydro-7β-hydroxy-2(1H)-phenanthrone, m.p. 107°–108° C. when recrystallized from acetone.

Further elution of the column with ether-methanol (19:1) afforded 0.9 g. of 1,2,3,4,4aα,4bβ,5,6,7,8-,8aα,9,10,10aβ-tetradecahydrophenanthrene-2α,7β-diol, m.p. 216°–218° C. when recrystallized from ether.

EXAMPLE 14

3,4,4aα,4bβ,5,6,7,8,8aα,9,10,10aβ-Dodecahydro-7α-hydroxy-2(1H)-phenanthrone

[X; 7α,4aα,4bβ,8aα,10aβ-configuration].

Using the reduction procedure described in Example 13,4,4aα,4bβ,5,6,7,8,8aα,9,10-decahydro-7α-hydroxy-2(3H)-phenanthrone (Example 10) (3.2 g., 0.014 mole) afforded 1.49 g. of 3,4,4aα,4bβ,5,6,7,8-,8aα,9,10,10aβ-dodecahydro-7α-hydroxy-2(1H)-phenanthrone, m.p. 137.5°–138° C. when recrystallized from ether.

3,4,4aα,4bβ,5,6,7,8,8aα,9,10,10aβ-Dodecahydro-7α-hydroxy-2(1H)-phenanthrone can be caused to react with methylmagnesium bromide to give 1,2,3,4,4aα,4bβ,5,6,7,8,8aα,9,10,10aβ-tetradecahydro-2-methyl-2,7α-dihydroxyphenanthrene, and the latter oxidized with chromic oxide to give 3,4,4aα,4bβ,5,6,7,8,8aα,9,10,10aβ-dodecahydro-7-methyl-7-hydroxy-2(1H)-phenanthrone [III; R' and R'' are H, X is H$_2$, Z is (HO)(CH$_3$)C].

3,4,4aα,4bβ,5,6,7,8,8aα,9,10,10aβ-Dodecahydro-7β-hydroxy-2(1H)-phenanthrone can be ketalized with ethylene glycol and the resulting ketal caused to react with sodium to give the sodio derivative of the 7α-hydroxy group which in turn can be caused to react with methyl iodide to give the 7-methoxy compound. Hydrolysis of the ketal then gives 3,4,4aα,4bβ,5,6,7,8-,8aα,9,10,10aβ-dodecahydro-7α-methoxy-2(1H)-phenanthrone [III; R' and R'' are H, X is H$_2$, Z is (α—CH$_3$O)CH].

3,4,4aα,4bβ,5,6,7,8,8aα,9,10,10aβ-Dodecahydro-7α-hydroxy-2(1H)-phenanthrone can be caused to react with p-toluenesulfonyl chloride in pyridine to give the 7α-p-toluenesulfonate, and the latter treated with anhydrous potassium fluoride in diethylene glycol, eighteen hours at 110° C., to give 3,4,4aα,4bβ,5,6,7,8-,8aα,9,10,10aβ-dodecahydro-7β-fluoro-2(1H)-phenanthrone [III; R' and R'' are H, X is H$_2$, Z is (β-F)CH]. By analogous procedures the corresponding 7β-chloro and 7β-bromo compounds can be prepared.

EXAMPLE 15

3,4,4aα,4bβ,5,6,7,8,8aβ,9,10,10aβ-Dodecahydro-7α-hydroxy-2(1H)-phenanthrone

[X; 7α,4aα,4bβ,8aβ,10aβ-configuration].

using the lithium-ammonia procedure of Example 13 for reduction, 4,4aα,4bβ,5,6,7,8,8aβ,9,10-decahydro-7α-hydroxy-2(3H)-phenanthrone (Example 8) (5.5 g., 0.025 mole) afforded 2.7 g. of 3,4,4aα,4bβ,5,6,7,8-,8aβ,9,10,10aβ-dodecahydro-7α-hydroxy-2(1H)-phenanthrone, m.p. 82°–83° C. when recrystallized from ether containing hexane.

EXAMPLE 16

3,4,4aα,4bβ,5,6,7,8,8aα,9,10,10aβ-Dodecahydro-7β-hydroxy-2(1H)-phenanthrone amidinohydrazone.

A solution of 3.5 g. (0.016 mole) of 3,4,4aα,4bβ,5,6,7,8,8aα,9,10,10a β-dodecahydro-7β-hydroxy-2(1H)-phenanthrone (Example 13) in 50 ml. of methanol was added to 115 ml. of methanol containing 4.93 g. (0.036 mole) of aminoguanidine bi-carbonate and 12 ml. of concentrated hydrochloric acid. After standing at room temperature overnight, the reaction mixture was added to 1 liter of ether. A precipitate formed which was found to be crude aminoguanidine hydrochloride and was removed by filtration. Dilution of the filtrate with more ether then precipitated the desired product (3.28 g., 66%). Recrystallization was effected by adding ether to a methanolic solution of the solid, to give 3,4,4aα,4bβ,5,6,7,8,8aα,9,10,10aβ dodecahydro-7β-hydroxy-2(1H)-phenanthrone amidinohydrazone in the form of its hydrochloride salt, m.p. 245°–253° C. (evacuated tube).

EXAMPLE 17

3,4,4aα,4bβ,5,6,7,8,8aα,9,10,10aβ-Dodecahydro-7β-hydroxy-2(1H)-phenanthrone 2,2-ethylene dithioketal.

A solution of 4 g. (0.018 mole) of hydroxy ketone 3,4,4aα,4bβ,5,6,7,8,8aα,9,10,10aβ-dodecahydro-7β-hydroxy-2(1H)-phenanthrone (Example 13) in 50 ml. of glacial acetic acid was treated with 5 ml. of ethane dithiol. The mixture was warmed slightly to effect solution and 4 ml. of boron trifluoride etherate was added to the warm solution. After the mixture had stood at room temperature for 5 minutes, water was added and the preciptated solid was collected. The solid (4.5 g.) was dissolved in 100 ml. of 5% methanolic potassium hydroxide containing 5% water and the mixture was boiled under reflux for 30 minutes. The volume of methanol was reduced by warming in vacuo and ice water was added. The precipitate was recrystallized from acetone and afforded 2.94 g. of 3,4,4aα,4bβ,5,6,7,8,8aα,9,10,10aβ-dodecahydro-7β-hydroxy-2(1H)-phenanthrone 2,2-ethylene dithioketal, m.p. 129°–130° C.

EXAMPLE 18

3,4,4aα,4bβ,5,6,7,9,10,10aβ-Decahydro-7-oxo-2(1H)-phenanthrone [III; R' and R'' are H, X is H$_2$, Z is C=C, $\Delta^8$].

A solution of 5.14 g. (0.023 mole) of 4,4aα,4bβ,5,6,7,8,8aα,9,10-decahydro-7β-hydroxy-2(3H)-phenanthrone (Example 9) in 50 ml. of pyridine was added to 50 ml. of pyridine containing 5.15 g. of chromium trioxide. After being stirred overnight the reaction mixture was added to 500 ml. of ethyl acetate. The mixture was filtered and the solvent was removed by warming in vacuo. Ether (150 ml.) was added and more solid was filtered off. The solvent was evaporated leaving 4.69 g. of an oily residue that crystallized. Recrystallization from ether afforded 3.27 g. (63%) of 3,4,4aα,4bβ,5,6,7,9,10,10aβ-decahydro-7-oxo-2(1H)-phenanthrone, m.p. 124°–125° C.

EXAMPLE 19

1,2,3,4,4aα,4bβ,5,6,7,8,8aα,9,10,10aβ-Tetradecahydrophenanthrene-2,7-dione.

A solution of 3.2 g. (0.014 mole) of 1,2,3,4,4aα,4bβ,-5,6,7,8,8aα,9,10,10aβ-tetradecahydrophenanthrene-2α,7β-diol (Example 11b) in 60 ml. of pyridine was added to 60 ml. of pyridine containing 6.4 g. of chromium trioxide. After being stirred overnight the reaction mixture was added to 600 ml. of ethyl acetate. The mixture was filtered and the solvent was removed by warming in vacuo. Ether (150 ml.) was added and more solid was removed by filtration. Upon concentration of the ether, there was obtained 1.51 g. of 1,2,3,4,4aα,4bβ,5,6,7,8,8aα,9,10,10aβ-tetradecahydrophenanthrene-2,7-dione, m.p. 152.5°–154° C. Upon further concentration, another 0.7 g., m.p. 149.5°–151.5° C. was obtained.

EXAMPLE 20

1,2,3,4,4aα,4bβ,5,6,7,8,8aα,9,10,10aβ-Tetradecahydrophenanthrene-2,7-dione bisamidinohydrazone.

A solution of 4.83 g. (0.022 mole) of 1,2,3,4,4aα,4bβ,5,6,7,8,8aα,9,10,10aβ-tetradecahydrophenanthrene-2,7-dione in 75 ml. of methanol was added to a solution of 13.6 g. (0.100 mole) of aminoguanidine bicarbonate and 35 ml. of concentrated hydrochloric acid in 315 ml. of methanol. After 24 hours at room temperature, the mixture was filtered to give 6.46 g. (73%) of 1,2,3,4,4aα,4bβ,5,6,7,8,8aα,9,10,10aβ-tetradecahydrophenanthrene-2,7-dione bisamidinohydrazone, m.p. 350° C.

EXAMPLE 21

3,4,4aα,4bβ,5,6,7,8,8aα,9,10;10aβ-Dodecahydro-7,7-ethylenedimercapto-2(1H)-phenanthrone

[III; R' and R'' are H, X is H$_2$, Z is (ethylenedithio)C].

A solution of 2.83 g. (9.4 mmoles) of 3,4,4aα,4bβ,5,6,7,8,8aα,9,10,10aβ-dodecahydro-7β-hydroxy-2(1H)-phenanthrone 2,2-ethylene dithioketal (Example 17) in 40 ml. of pyridine was added to 40 ml. of pyridine containing 3 g. of chromium trioxide. After 5 days at room temperature the reaction mixture was added to 500 ml. of ethyl acetate. The mixture was filtered and the filtrate was concentrated to a residue by warming in vacuo. Ether (200 ml.) was added to the residue and more unwanted solid was separated. The ether was concentrated and 2 g. of 3,4,4aα,4bβ,5,6,7,8,8aα,9,10,10aβ-dodecahydro-7,7-ethylenedimercapto-2(1H)-phenanthrone, m.p. 131°–132° C. was obtained from the mother liquor (yield 76%).

EXAMPLE 22

Lithium-ammonia reduction of 2.04 g. of 4,4aα,4bβ,5,6,7,8,8aα,9,10-decahydro-7β-hydroxy-4bβ-methyl-2(3H)-phenanthrone according to the procedure described above in Example 13 afforded 0.99 g. of 3,4,4aα,4bβ,5,6,7,8,8aα,9,10,10aβ-dodecahydro-7β-hydroxy-4bα-methyl-2(1H)-phenanthrone [III; R' is CH$_3$, R'' is H, X is H$_2$, Z is (β-HO)CH], m.p. 105°–107° C. and a second crop of 0.1 g., m.p. 103°–105° C. (54%).

1,2,3,4,4aα,4b,5,6,7,8,8aα,9,10,10aβ-Tetradecahydro-4bβ-methylphenanthrene-2α,7β,-diol (0.19 g., m.p. 171°–175° C.) was also isolated (9%). Recrystallization from acetonitrile afforded a sample that melted at 182°–184° C. This compound can be oxidized to the corresponding 2,7-dione.

EXAMPLE 23

1β,4bβ-Dimethyl-3,4,4aα,4b,5,6,7,8,8aα,9,10,10aβ-dodecahydro-7β-hydroxy-2(1H)-phenanthrone

[III; R' and R'' are CH$_3$, X is H$_2$, Z is (β-HO)CH].

Dry liquid ammonia was prepared by treatment of 300 ml. of liquid ammonia with lithium wire until the blue color persisted, followed by distillation until 100 ml. of liquid ammonia had been condensed in the reaction vessel. To the dry liquid ammonia was added with stirring 0.16 g. (23 mmoles) of lithium wire followed by dropwise addition of a solution of 1.00 g. (4.29 mmoles) of 4,4aα,4b,5,6,7,8,8aα,9,10-decahydro-7β-hydroxy-4bβ-methyl-2(3H)-phenanthrone in 15 ml. of tetrahydrofuran and 35 ml. of anhydrous ether over a 10 minute period. The mixture was stirred for 30 minutes and then treated with 1.2 ml. of methyl iodide which immediately discharged the blue color. The ammonia was allowed to evaporate and the residue was treated with 100 ml. of water and extracted with 250 ml. of ether. The extract was washed with water and saturated salt solution and dried ($MgSO_4$). The residue (1.05 g.), obtained upon evaporation of the solvent, was chromatographed on 30 g. of silica gel. Elution with 1:1:3 methylene dichloride-ether:pentane afforded crystalline material which, upon recrystallization from acetonitrile, furnished 0.34 g. of product, m.p. 115°–120° C. Recrystallization of the latter from acetonitrile gave 1β,4bβ-dimethyl-3,4,4aα,4b,5,6,7,8,8aα,9,10,10aβ-dodecahydro-7β-hydroxy-2(1H)-phenanthrone, m.p. 129–132° C.

EXAMPLE 24

4,4aα,4bβ,5,6,7,8,8aα,9,10-Decahydro-7α,10′-dihydroxy-2(3H)- phenanthrone [XII; 7α-OH] and 1,2,3,4,4aα,4a,5,6,7,9,10,10aβ-dodecahydro-7-oxophenanthrene-2α,4bβ-diol [XIII; 2α-OH].

The microorganism, Cunninghamella bainieri (American Type Culture Collection No. 9244) was grown in surface growth 15 days old agar slants at 26° C. containing as a nutrient medium:

(A)
Maltose 40 gr.
Proteose peptone 10 gr.
Agar 15 gr.
Distilled water to 1 liter, and suspended in distilled water. Five ml. portions of the suspension were used to inoculate 500 ml. Erlenmeyer flasks each containing 100 ml. of a sterilized medium (autoclaved at 15 lbs. per sq. in. for 20 minutes) containing:

(B)
Cerelose (glucose) 5%
Edamine (An enzymatic hydrolysate 2% of milk protein (Sheffield Farms Co.)
Cornsteep 0.5%
Tap water to 1 liter The seeded Erlenmeyer flasks were grown for 72 hours at 26° C. on a shaker rotating at 210 cycles per minute. Fourteen-liter jar fermentors were prepared, each containing 10 liters of sterile medium B (sterilized for 45 minutes at 15 lbs. pressure) described above, and seeded with 10% quantities of inocula. The inoculated fermentors were agitated at 400 r.p.m. and aerated with an air supply of 4 liters of air per minute at a temperature of 27° C. for 48 hours. After this period of time, a solution of 3 gr. of 4,4aα,4bβ,5,6,7,8,8aα,9,10-decahydro-7β-hydroxy-2(3H)- phenanthrone (Example 9) dissolved in 15 ml. of N,N-dimethylformamide was added to each tank. Antifoam was added as needed during the fermentation cycle.

Samples were taken from the tanks every 24 hours and analyzed chromatographically. Further incubation for 144 hours after addition of the substrate indicated that this material had disappeared and the formation of three more polar metabolites was observed. The fermentation was terminated and the whole fermentation mash adjusted to pH 4.0 with 50% hydrochloric acid and extracted twice with 10-liter portions of methylene dichloride. The extracts were combined and concentrated under reduced pressure to a residue. This residue was triturated twice with 250-ml. portions of n-pentane to remove some oils. The pentane washed fermentation extract (43 g.) from 21 g. of substrate was dissolved in ethyl acetate and put on 2 kg. of silica gel. The column was eluted with ethyl acetate. The first 8 liters eluted brown oils which were discarded. The next 7.5 liters of ethyl acetate eluted 4.38 g. of a mixture of hydroxylated products. Continued elution with ethyl acetate afforded 5.98 g. of oil containing mostly the more polar 4,4aα,4bβ,5,6,7,8,8aα,9,10-decahydro-7β,10α-dihydroxy-2(3H)-phenanthrone. After preparative thick layer chromatography of these two fractions 1.45 g. of 4,4aα,4bβ,5,6,7,8,8aα,9,10-decahydro-7β,10α-dihydroxy-2(3H)-phenanthrone was obtained, m.p. 143°–146° C. Recrystallization from acetone containing ether gave a sample with m.p. 155°–156° C.

From the less polar band 1 g. of 1,2,3,4,4aα,4bβ,5,6,7,9,10,10aβ-dodecahydro-7-oxophenanthrone-2α,4bβ-diol, m.p. 151°–154° C. was obtained. THis material was recrystallized from acetone containing ether to give a sample with m.p. 163°–165° C. indistinguishable by infrared analysis, TLC analysis and mixed melting point from a sample prepared by an alternative chemical method as described below.

By substituting as the substrate in the foregoing preparation, 4,4aα,4b,5,6,7,8,8aα,9,10-decahydro-7β-hydroxy-4bβ-methyl-2(1H)-phenanthrone (XI), there can be obtained 4,4aα,4b,5,6,7,8,8aα,9,10-decahydro-4bβ-methyl-7β,10α-dihydroxy-2(3H)-phenanthrone.

In the foregoing fermentation process, the organism Cunninghamella bainieri can be replaced by Cunninghamella verticillator or Cunninghamella elegans.

EXAMPLE 25 a.

1,2,3,4,4aα,5,6,7,8,9,10,10aβ-Dodecahydro-7-oxo-2α-phenanthrol.

A solution of 13.8 g. (0.06 mole) of 1,2,3,4,4aα,9,10,10aα-octahydro-7-methoxy-2β-phenanthrol and -2α-phenanthrol in 50 ml. of tetrahydrofuran was added to 300 ml. of liquid ammonia. Lithium wire (4.7 g., 0.66 mole) was added over a half-hour period with stirring. After stirring the mixture for a half-hour longer, a mixture of 70 ml. of absolute ethanol and 70 ml. of ether (anhydrous) was added to discharge the blue color. The solution was evaporated to half the volume. Ether and water were added and, after shaking, the layers were separated. The ether was washed with saturated sodium chloride solution and the aqueous layers were washed with a fresh portion of ether. The combined ether layers were dried ($Na_2SO_4$) and the ether was removed by warming in vacuo. The remaining residue was taken up in 100 ml. of tetrahydrofuran and 200 ml. of methanol. Oxalic acid (10 g.) in 75 ml. of water was added. The solution was kept at room temperature for 75 minutes and then added to a large volume of ether. The layers were separated and the ether layer was washed several times with saturated sodium bicarbonate solution. The aqueous layers were washed with a fresh portion of ether. The combined ether layers were dried ($Na_2SO_4$) and the solvent was removed by warming in vacuo. The residue crystallized from ether containing hexane and afforded 7.9 g. of 1,2,3,4,4aα,5,6,7,8,9,10,10aβ-dodecahydro-7-oxo-2α-phenanthrol, m.p. 120°–123° C.

b.
1,2,3,4,4aα,4b,5,6,7,9,10,10aβ-Dodecahydro-7-oxophenanthrene-2α,4bβ-diol

[XIII; 2 -OH] and -2α,4bα-diol.

A solution of 6.76 g. of 85% m-chloroperbenzoic acid in 80 ml. of methylene dichloride was added to 1,2,3,4,4aα,5,6,7,8,9,10,10aβ-dodecahydro-7-oxo-2α-phenanthrol (6.5 g., 0.29 mole) in 50 ml. of methylene dichloride. After standing at room temperature overnight, the reaction mixture was washed twice with saturated sodium bicarbonate solution and once with saturated sodium chloride solution. The aqueous layers were washed again with methylene dichloride. The organic layers were combined and dried with sodium sulfate. The solvent was removed by warming in vacuo, leaving 6.3 g. of an oily residue that would not crystallize. The residue was chromatographed on 500 g. of silica gel. Ethyl acetate with 0.5% methanol was used for elution. A less polar fraction (2.53 g.) was obtained which on crystallization and recrystallization from acetone containing hexane, afforded 1.43 g. of 1,2,3,4,4aα,4b,5,6,7,9,10,10aβ-dodecahydro-7-oxo-phenanthrene-2α,4bβ-diol, m.p. 160°–161° C.

A more polar fraction (1.74 g.) afforded, on crystallization and recrystallization from acetone-hexane, 0.88 g. of 1,2,3,4,4aα,4b,5,6,7,9,10,10aβ-dodecahydro-7-oxo-phenanthrene-2α,4bα-diol, m.p. 176°–177° C.

EXAMPLE 26
1,2,3,4,4aα,4bβ,5,6,7,8,8aα,9,10,10aβ-Tetradecahydro-7β-acetoxyphenanthrene-2,10-dione

[III; R' and R'' are H, X is O, Z is (β-CH₃COO)CH].

A slution of 900 mg. of 4,4aα,4bβ,5,6,7,8,8aα,9,10-decahydro-7β,10°-dihydroxy-2(3H)-phenanthrone (Example 24) in 50 ml. of acetic acid and 5 ml. of 10% sulfuric acid was kept at room temperature in a nitrogen atmosphere for 24 hours. At the end of this time the solution was poured into ice and solid sodium bicarbonate was added. Ether was added and the layers were separated. The ether was washed with saturated sodium bicarbonate solution and then with saturated sodium chloride solution. The aqueous layers were washed with more ether. The ether was combined and dried over sodium sulfate. The ether was evaporated by warming in vacuo leaving a residue that partially crystallized. Ether containing hexane was added and 310 mg. of 1,2,3,4,4aα,4bβ,5,6,7,8,8aα,9,10,10aβ-tetradecahydro-7β-acetoxyphenanthrene-2,10-dione. Recrystallization from ether gave a sample with m.p. 146°–148° C.

EXAMPLE 27
1,2,3,4,4aα,4b,5,6,7,9,10,10aβ-Dodecahydro-4bβ-hydroxyphenanthrene-2,7-dione

[III; R' is OH, R'' is H, X is H₂, Z is O=C, Δ⁸].

A solution of 1,2,3,4,4aα,4b,5,6,7,9,10,10aβ-dodecahydro-7-oxophenanthrene-2α,4bβ-diol (Example 24) in 35 ml. of pyridine was added to 35 ml. of pyridine containing 3 g. of chromium trioxide. After standing at room temperature overnight, the reaction mixture was diluted with a large volume of ethyl acetate and filtered. The solvent was removed by warming in vacuo. The residue was taken up in acetone ether and was filtered. The volume was reduced and there was obtained 2 g. of 1,2,3,4,4aα,4b,5,6,7,9,10,10aβ-dodecahydro-4bβ-hydroxyphenanthrene-2,7-dione, m.p. 179°–180° C. when recrystallized from ether.

EXAMPLE 28 a.
3,4,4aα,4b,5,6,7,8,8aα,9,10,10aβ-Dodecahydro-7β-hydroxy-4bβ-methyl-2(1H)-phenanthrone 7-p-toluenesulfonate.

A solution of 10.0 g. (0.043 mole) of 3,4,4aα,4b,5,6,7,8,8aα,9,10,10aβ-dodecahydro-7β-hydroxy-4bβ-methyl-2(1H)-phenanthrone (Example 22) in 50 ml. of pyridine was treated with 9.60 g. (0.050 mole) of p-toluenesulfonyl chloride in 50 ml. of pyridine and kept overnight at room temperature. The mixture was added to 150 ml. of concentrated hydrochloric acid and 350 ml. of ice-water and the mixture was extracted with ether. The extract was washed with 2N sodium hydroxide solution, dried (MgSO₄) and concentrated to a residue to give 16.4 g. of 3,4,4aα,4b,5,6,7,8,8aα,9,10,10aβ-dodecahydro-7β-hydroxy-4bβ-methyl-2(1H)-phenanthrone 7-p-toluenesulfonate as an amber oil. This oil was used without further purification in the following procedure.

b. Detosylation of 3,4,4aα,4b,5,6,7,8,8aα,9,10,10aβ-dodecahydro-7β-hydroxy-4bβ-methyl-2(1H)-phenanthrone 7-p-toluenesulfonate.

A solution of 16.3 g. of the above oily tosylate in 100 ml. of s-collidine was heated under reflux for 4 hours. The solution was cooled and poured into 400 ml. of 2N sulfuric acid. The acid mixture was extracted with ether and the extract was washed with 2N sulfuric acid, water and brine. It was dried (MgSO₄) and concentrated to a residue to give 7.0 g. of an oil which was assumed to be a mixture of Δ⁶- and Δ⁷-2-phenanthrones. This mixture was hydrogenated in the following procedure without purification.

c. Hydrogenation of the mixture of Δ⁶- and Δ⁷-2-phenanthrones.

A solution of 0.69 g. of the mixture of phenanthrones described in the preceding example in 25 ml. of undenatured ethanol was treated with 0.10 g. of 10% palladium-on-charcoal and the mixture was shaken in a hydrogen atmosphere until one molar equivalent was absorbed (5 minutes). The mixture was filtered and the filtrate was concentrated to a residue by warming under reduced pressure. THe residue was dissolved in ether and the solution was dried (MgSO₄) and concentrated to give 0.56 g. of 3,4,4aα,4b,5,6,7,8,8aα,9,10,10aβ-dodecahydro-4bβ-methyl-2(1H)-phenanthrone [III; R' is CH₃, R'' is H, X is H₂, Z is CH₂] as an amber oil. It was purified by column chromatography on 15 g. of silica gel with elution by 1:9 ether-pentane.

EXAMPLE 29 a.
8,8-Dimethyl-1,2,3,4,4aα,4bβ,5,6,7,8,10,10aβ-dodecahydro-7-oxo-2α-phenanthrol [XV; R' is H, lower-alkyl is CH₃].

A solution of 27.4 g. (0.125 mole) of 4,4aα,4bβ,5,6,7,8,8aα,9,10-decahydro-7β-hydroxy-2(3H)-phenanthrone (IX) (Example 9) in 600 ml. of t-butanol was treated with 35 g. (0.310 mole) of potassium t-butoxide. The reaction mixture was flushed with nitrogen. Methyl iodide (70 g., 0.500 mole) was added over a half-hour period. The solution was stirred at room temperature for one hour and was finally heated under reflux for 10 minutes. The reaction mixture was cooled and dilute hydrochloric acid was added. Ether and water were added and the layers were separated. The ether was washed with dilute sodium hydroxide and then saturated sodium chloride solution. The ether was dried (Na$_2$SO$_4$) and evaporated –afford an oily residue that crystallized from ether containing hexane. Recrystallization twice from the same solvent gave 11.0 g. of 8,8-dimethyl-1,2,3,4,4aα,4bβ5,6,7,8,10,10aβ-dodecahydro-7-oxo-2α-phenanthrol, m.p. 116°–118° C. Upon concentration of the mother liquor another crop of 3.2 g., m.p. 114°–116° C. was obtained. The mother liquor was chromatographed on 500 g. of silica gel. Elution wlith methylene dichloride-ether-pentane (2:5:3) afforded another 5.5 g., m.p. 116°–117° C. (64%). A sample recrystallized from ether containing hexane melted at 121°–122° C.

b. 3,4,4aα,4bβ,5,6,7,8,10,10aβ-Decahydro-8,8-dimethyl-7-oxo-2(1H)-phenanthrone

[XVI; R″ is H, lower-alkyl is CH$_3$].

A solution of 16.6 g. (0.067 mole) of the hydroxy ketone of part (a) in 210 ml. of pyridine was added to 210 ml. of pyridine containing 16.6 g. (0.166 mole) of chromium trioxide. The mixture was stirred overnight and was taken then added to about 700 ml. of ethyl acetate. The mixture was filtered through infusorial earth and the solvent was removed by warming in vacuo. Ether was added to the residue and more inorganic solids were filtered away. The ether was concentrated to afford 11.9 g. of 3,4,4aα,4bβ,5,6,7,8,10,10aβ-decahydro-8,8-dimethyl-7-oxo-2(1H)-phenanthrone, m.p. 130°–133° C. A second crop of 1.21 g., m.p. 128°–130° C. was also obtained. The mother liquor was chromatographed on 150 g. of silica gel. Elution with methylene dichloride-ether-pentane (2:3:5) afforded another 0.7 g., m.p. 131°–133° C. (83%). A sample recrystallized from ether melted at 133°–134° C.

Similarly, starting from 1,2,3,4,4aα,4b,5,9,10,10aβ-decahydro-2α-hydroxy-4bβ-methyl-7(6H)-phenanthrone [XIV; R′ is CH$_3$], there can be prepared 3,4,4aα,4b,5,6,7,8,10,10aβ-decahydro-4bβ,8,8-trimethyl-7-oxo-2(1H)-phenanthrone [XVI; R′ is CH$_3$, lower-alkyl is CH$_3$]. 3,4,4aα,4b,5,6,7,8,10,10aβ-Decahydro-4bβ,8,8-trimethyl-7-oxo-2(1H)-phenanthrone reacts with ethylene glycol in the presence of p-toluenesulfonic acid to give the 2-mono-ethylene glycol ketal. The latter ketal is reduced with lithium aluminum hydride to give 3,4,4aα,4b,5,6,7,8,10,10aβ-decahydro-4bβ,8,8-trimethyl-7β-hydroxy-2(1H)-phenanthrone 2-mono-ethylene glycol ketal, which is further reduced catalytically in the presence of palladium-on-carbon to give 3,4,4aα,4b,5,6,7,8,8aα,9,10,10aβ-dodecahydro-4bβ,8,8-trimethyl-7β-hydroxy-2(1H)-phenanthrone 2-mono-ethylene glycol ketal. The ketal is then cleaved by heating it with acetic acid to give 3,4,4aα,4b,5,6,7,8,8aα,9,10,10aβ-dodecahydro-4bβ,8,8-trimethyl-7β-hydroxy-2(1H)-phenanthrone [XVIII; R′ is CH$_3$, lower-alkyl is CH$_3$], m.p. 112°–117° C. when recrystallized from isopropyl alcohol.

EXAMPLE 30 a. Mixture of 10α- and 10β-acetoxy-8,8-dimethyl-3,4,4aα,4bβ,5,6,7,8,10,-10aβ-decahydro-7-oxo-2(1H)-phenanthrones.

A solution of 250 mg. (1.0 millimoles) of 3,4,4aα,4bβ,5,6,7,8,10,10aβ-decahydro-8,8-dimethyl-7-oxo-2(1H)-penanthrone in 5 ml. of benzene and 1 ml. of glacial acetic acid was treated with 0.17 ml. (1.0 millimoles) of t-butyl peracetate (75% in benzene). Cuprous chloride (1 mg.) was added and oxygen was removed from the reaction mixture by flushing it with nitrogen The solution was heated under reflux in an atmosphere of nitrogen for 22 hours. Another 0.17 ml. (1.0 millimoles) of t-butyl peracetate and a trace of cuprous chloride were added. After the reaction mixture was heated under reflux for another 7 hours, the above addition procedure was repeated. The reaction mixture was then heated under reflux for 24 hours. The reaction mixture was added to ice water. Ether was added and the layers were separated. The ether was washed with saturated sodium bicarbonate and saturated sodium chloride solutions and then dried (Na$_2$SO$_4$). Evaporation of the solvent afforded an oily residue that was redissolved in ether and filtered. Evaporation of the solvent by warming in vacuo gave 190 mg. of an oily residue. This residue was chromatographed on 19 g. of silica gel. Elution with 400 ml. of methylene dichloride-ether-pentane (2:3:5) gave 50 mg. (20%) of starting diketone. Continued elution with another 60 ml. of the same solvent mixture afforded 60 mg. (20%) of the mixture of 10α- and 10β-acetates.

b. Mixture of 10α- and 10β-acetoxy-8,8-dimethyl-1,2,3,4,4aα,4bβ,5,6,7,8,10,-10aβ-dodecahydro-2α-phenanthrol.

A solution of 2.3 g. (9.3 millimoles) of 8,8-dimethyl-1,2,3,4,4aα,4bβ,5,6,7,8,10,10aβ-dodecahydro-7-oxo-2α-phenanthrol in 50 ml. of benzene and 5 ml. of acetic acid was treated with 1.7 ml. (10.0 millimoles) of t-butyl peracetate (75% in benzene). Cuprous chloride (10 mg.) was added and the reaction flask after being flushed with nitrogen was boiled under reflux in a nitrogen atmosphere for 24 hours. Another 2 ml. of t-butyl peracetate was added and the reaction mixture was boiled under reflux for another 24 hours. The reaction mixture was worked up as described above in part (a). The oily residue (2.65 g.) was chromatographed on 200 g. of silica gel. Elution with methylene dichloride-ether-pentane (2:3:5) afforded 540 mg. (23%) of starting material. Continued elution with methylene dichloride-ether (1:4) then gave 690 mg. (19%) of the mixture of acetates.

EXAMPLE 31

8,8-Dimethyl-3,4,4aα,4bβ,5,6,7,8,10,10aβ-Decahydro-7,10-dioxo-2(1H)-phenanthrone

[XVII; R′ is H, lower-alkyl is Ch$_3$].

a. The mixture of acetates from parts (a) and (b) of Example 30 were combined and were dissolved in 30 ml. of 5% methanolic potassium hydroxide containing 5% water. The solution was boiled under reflux in a nitrogen atmosphere for 45 minutes. The reaction mixture was added to ice and water. Sodium chloride was added followed by ether. The layers were separated. The ether was washed twice with saturated sodium chloride solution. The aqueous layers were washed with a fresh portion of ether and the combined ether layers were then dried (Na$_2$SO$_4$) and evaporated by warming in vacuo to afford 390 mg. of an oily residue. The residue, containing a mixture of 10α- and 10β-hydroxy-8,8-dimethyl-3,4,4aα,4bβ,5,6,7,8,10,10aβ-decahydro-7-oxo-2(1H)-phenanthrones and 10α- and 10β-hydroxy-8,8-dimethyl-1,2,3,4,4aα,4bβ,5,6,7,8,10,10aβ-dodecahydro-2α-phenanthrols was dissolved in 20 ml. of pyridine and this solution was added to 20 ml. of pyridine containing 600 mg. of chromium trioxide. The reaction mixture was kept at room temperature for 40 hours and then added to about 100 ml. of ethyl acetate. The mixture was filtered and warmed in vacuo to remove the solvent. Ether was added and more inorganic solids were filtered away. The ether was evaporated. The residue was crystallized from ether and afforded 140 mg. of 8,8-dimethyl-3,4,4aα,4bβ,5,6,7,8,10,10aβ-decahydro-7,10-dioxo-2(1H)-phenanthrone, m.p. 147°–150° C. (23%). Recrystallization from ether gave a sample melting at 152°–153° C.

b. A solution of 19 ml. of t-butyl chromate in carbon tetrachloride, 20 ml. of carbon tetrachloride, 6 ml. of acetic acid and 2.5 ml. of acetic anhydride were heated at 50° C. in a water bath. A slow stream of air was blown through the solution while it was being stirred. A solution of 1 g. (4.1 millimoles) of 3,4,4aα,4bβ,5,6,7,8,10,10aβ-decahydro-8,8-dimethyl-7-oxo-2(1H)-phenanthrone in 18 ml. of carbon tetrachloride was added during a half-hour period. The temperature was maintained at 50°–70° C. for a 2 hour period. This solution was stirred at room temperature with a slow stream of air passing through for another 16 hours. Carbon tetrachloride (50 ml.) was added to the reaction mixture (to maintain volume). Oxalic acid (7.5 g., 83 millimoles) in 75 ml. of water was added during a half-hour period while the solution was being stirred in an ice bath. Oxalic acid (5.25 g.) was again added and the reaction mixture was stirred for another 2 hours. More carbon tetrachloride and water were added and the layers were separated. The aqueous layer was washed with a fresh portion of carbon tetrachloride. The carbon tetrachloride solutions were combined and were washed twice with saturated sodium bicarbonate and once with saturated sodium chloride solution. The organic solution was dried (Na$_2$SO$_4$) and the solvent was removed by warming in vacuo to afford 320 mg. of a residue. The aqueous layers were extracted with ethyl acetate and gave another 570 mg. of oily residue upon evaporation. Crystallization from ether afforded 225 mg. of 8,8-dimethyl-3,4,4aα,4bβ,5,6,7,8,10,10aβ-decahydro-7,10-dioxo-2(1H)-phenanthrone, m.p. 148°–151° C.

EXAMPLE 32

Ethyl 3,4,4aα,4bβ,5,6,7,8,8aα-dodecahydro-7β-hydroxy-Δ$^{2(1H)}$, α-phenanthreneacetate (mixture of isomers) [I; R is C$_2$H$_5$, R°, R' and R'' are H, X is H$_2$, Z is (β-HO)CH].

A solution of sodium ethoxide [prepared from 1.6 g. (0.070 mole) of sodium and absolute ethanol] in 120 ml. of dry dimethylformamide (DMF) was cooled in an ice bath and treated dropwise with a solution of 15.5 g. (0.070 mole) of triethyl phosphonoacetate in 20 ml. of dry DMF with stirring. The resulting solution was stirred cold (0° C.) for 5 minutes and then a solution of 7.68 g. (0.0346 mole) of 7β-hydroxy-3,4,4aα,4bβ,5,6,7,8,8aα,9,10,10aβ-dodecahydro-2(1H)-phenanthrone (Example 13) in 30 ml. of dry DMF was added dropwise with stirring. This mixture was then stirred cold (0° C.) for 15 minutes and at room temperature for two hours. It was added to 1.5 liter of water and the mixture was made acidic with 2N hydrochloric acid. The precipitated product was extracted with ether and the extracts were washed with brine and dried over sodium sulfate. Removal of the ether gave an oily residue which partially crystallized upon addition of about 25 ml. of ethanol. Dilution of this mixture with 300 ml. of water and filtration afforded 10.4 g. of a crystalline product, m.p. 89°–101° C., which was shown by gas-liquid phase chromatography (glpc) to be a 1:1 mixture of cis and trans isomers together with 1.6% of an impurity. This mixture was purified on silica chromatoplates developed with pure ether and then recrystallized from ether-hexane to give ethyl 3,4,4aα,4bβ,5,6,7,8,8aα,9,10,10aβ-dodecahydro-7β-hydroxy Δ$^{2(1H)}$, α-phenanthreneacetate, m.p. 102°–110° C.

EXAMPLE 33

Methyl 1β,4bβ-dimethyl-3,4,4aα,4b,5,6,7,8,8aα,9,10,10aβ-dodecahydro-7β-hydroxy-Δ$^{2(1H)}$, α-phenanthreneacetate

[I; R is CH$_3$, R° is H, R' and R'' are CH$_3$, X is H$_2$, Z is (β-HO)CH].

To a suspension of 2.82 g. (0.052 mole) of reagent sodium methoxide in 35 ml. of dry 1,2-dimethoxyethane was added 9.5 g. (0.052 mole) of trimethyl phosphonoacetate in 35 ml. of dry 1,2-dimethoxyethane and the mixture was stirred for 1 hour at room temperature. A solution of 6.5 g. (0.026 mole) of 1β,4bβ-dimethyl-7β-hydroxy-3,4,4aα,4b,5,6,7,8,8aα,9,10,-10aβ-dodecahydro-2(1H)-phenanthrone (Example 23) in 70 ml. of 1,2-dimethoxyethane was added. Silica plates developed with methanol-ether (1:49) showed that the reaction was about 50% complete in one hour but that it progressed no further even when the mixture was refluxed (84° C.) for 5 days. After the reflux period, 25 ml. of water and 500 ml. of ether were added and the layers were separated. The organic layer was washed with brine, dried over magnesium sulfate and concentrated to give 9.0 g. of methyl 1β,4bβ-dimethyl-3,4,4aα,4b,5,6,7,8,8aα,9,10,10aβ-dodecahydro-7β-hydroxy-Δ$^{2(1H)}$, α-phenanthreneacetate as a viscous oil which contained considerable unreacted ketone. This mixture was hydrolyzed directly, giving a carboxylic acid which was easily separable from ketonic impurity.

EXAMPLE 34 a. Ethyl 3,4,4aα,4bβ,5,6,7,8,8aα,9,10,10aβ-dodecahydro-7-oxo-Δ$^{2(1H)}$, α-phenanthreneacetate (Isomer A)

[I; R is C$_2$H$_5$, R°, R' and R'' are H, X is H$_2$, Z is O C].

A solution of 25.4 g. (0.087 mole) of ethyl 3,4,4aα,4bβ,5,6,7,8,8aα,9,10,10aβ-dodecahydro-7β-dydroxy-Δ$^{2(1H)}$, α-phenanthreneacetate (Example 32) in 220 ml. of pyridine was added in 2 minutes with stirring to a mixture of 21.9 g. (0.22 mole) of chromium trioxide and 220 ml. of pyridine at room temperature and the resulting mixture was stirred overnight. Ethyl acetate (1.5 liter) was added, the mixture was filtered and the flitrate was concentrated to a residue by warming under reduced pressure. This residue was treated with 400 ml; of ether and further insoluble material was removed by filtration. Concentration of the ether solution and addition of hexane afforded 6.13 g. of ethyl 3,4,4aα, 4bβ,5,6,7,8,8aα,9,10,10aβ-dodecahydro-7-oxo-Δ$^{2(1H),\alpha}$ -phenanthreneacetate (Isomer A), m.p. 95°–96.5° C. when recrystallized from ether-hexane.

b. 3,4,4aα,4bβ,5,6,7,8,8aα,9,10,10aβ-Dodecahydro-7-oxo-Δ$^{2(1H),\alpha}$ -phenanthreneacetic acid (Isomer B) [I; R, R°, R' and R'' are H, X is $H_2$, Z is O=C].

The mother liquor residues from the preceding experiment containing ethyl 3,4,4aα,4bβ,5,6,7,8-,8aα,9,10,10aβ-dodecahydro-7-oxo-Δ$^{2(1H),}$ α-phenanthreneacetate were dissolved in 500 ml. of 95% ethanol, 200 ml. of 2N aqueous sodium hydroxide was added and the solution was refluxed in a nitrogen atmosphere for 75 minutes. The reaction mixture was added to ice-water, neutralized with acetic acid and the product was extracted with ether. The ether extracts were extracted with 2N sodium hydroxide and these extracts acidified with 2N hydrochloric acid. The precipitated carboxylic acid was collected and recrystallized from ethyl acetate to give 4.36 g. of 3,4,4aα,4bβ,5,6,7,8-,8aα,9,10,10aβ-dodecahydro-7-oxo-Δ$^{2(1H),}$ α-phenanthreneacetic acid (Isomer B), m.p. 220°–222° C. (vac.) when recrystallized from ethyl acetate.

c. Methyl 3,4,4aα,4bβ,5,6,7,8,8aα,9,10,10aβ-dodecahydro-7-oxo-Δ$^{2(1H),}$ α-phenanthreneacetate (Isomer B) [I; R is $CH_3$, R°, R' and R'' are H, X is $H_2$, Z is O=C].

The mother liquor residues from separation of the Isomer B acid described immediately above contained 8,22 g. (0.0313 mole) of a mixture of Isomer A and Isomer B unsaturated carboxylic acids. This solid, m.p. 180°–195° C., was dissolved in 250 ml. of methanol, 0.10 mole of diazomethane in ether was added and the solution was allowed to stand overnight. The solvent was removed and the crystalline residue was recrystallized from ether by the addition of hexane to give 2.87 g. of material which melted at 100°–130° C. Two further recrystallizations furnished 1.6 g. of methyl 3,4,4aα,4bβ,5,6,7,8,8aα,9,10,10aβ-dodecahydro-7-oxo-Δ$^{2(1H),\alpha}$ -phenanthreneacetate (Isomer B), m.p. 139°–141° C.

EXAMPLE 35

Ethyl 1,2,3,4,4aα,4bβ,5,6,7,8,8aα,9,10,10aβ-tetradecahydro-7β-hydroxy-2-phenanathreneacetate (Isomer A)

[I; R is $C_2H_5$, R°, R' and R'' are H, X is $H_2$, Z is (β-HO)CH, saturated side chain].

A solution of 12.0 g. (0.041 mole) of ethyl 3,4,4aα,-4bβ,5,6,7,8,8aα,9,10,10aβ-dodecahydro-7β-hydroxy-Δ$^{2(1H),}$ α-phenanthreneacetate (Example 32) in 300 ml. of absolute ethanol was hydrogenated at 3.9 kg./cm³ and 25° C. for 2 and ½ hours in the presence of 1.2 g. of 10% palladium-on-carbon. The mixture was filtered and the filtrate was concentrated to a residue by warming under reduced pressure. The residue was dissolved in ether and precipitated by addition of a small amount of hexane to give 4.43 g. of material, m.p. 110°–11.5° C. Concentration of the filtrate gave 1.07 g.

of material, m.p 106°–108° C. (41%). Recrystallization from ether containing hexane afforded ethyl 1,2,3,4,4aα,4bβ,5,6,7,8,8aα,9,10,10aβ-tetradecahydro-7β-hydroxy-2-phenanthreneacetate (Isomer A), m.p. 110°–111° C.

The mother liquor residues were greatly enriched in Isomer B but TLC showed no separation of these isomers when using silica plates developed with 100% ether or 3:7 pentane-ether. These residues were hydrolyzed as described below in Example 53.

By the foregoing procedures the following examples of lower-alkyl esters (I; R is lower-alkyl) were prepared. In most instances the esters were not purified but were hydrolyzed directly to the corresponding free acids as described below.

EXAMPLE 36

Methyl 3,4,4aα,4bβ,5,6,7,8,8aα,9,10,10aβ-dodecahydro-4bβ-methyl-Δ$^{2(1H),}$ α-phenanthreneacetate [I; R is $CH_3$, R°, is H, R' is $CH_3$, R'' is H, X is $H_2$, Z is $CH_2$] from 3,4,4aα,4b,5,6,7,8,8aα,9,10,10aβ-dodecahydro-4bβ-methyl-2(1H)-phenanthrone (Example 28) and trimethyl phosphonoacetate.

EXAMPLE 37

Methyl 3,4,4aα,4bβ,5,6,7,8,8aα,9,10,10aβ-dodecahydro-7β-hydroxy-Δ$^{2(1H),}$ α-phenanthreneacetate [I; R is $CH_3$, R°, R' and R'' are H, X is $H_2$, Z is (β-HO)CH], from 7β-hydroxy-3,4,4aα,4bβ,5,6,7,8-,8aα,9,10,10,aβ-dodecahydro-2(1H)-phenanthrone (Example 13) and trimethyl phosphonoacetate.

EXAMPLE 38:

Ethyl 3,4,4aα4bβ,5,6,7,8,8aα,9,10,10aβ-dodecahydro-7α-hydroxy-Δ$^{2(1H),}$ α-phenanthreneacetate [I; R is $C_2H_5$, R°, R' and R'' are H, Z is (α-HO)CH], from 3,4,4aα,4bβ,5,6,7,8,8aα,9,10,10aβ-dodecahydro-7α-hydroxy-2(1H)-phenanthrone (Example 14) and triethyl phosphonoacetate.

EXAMPLE 39:

Methyl 3,4,4aα,4bβ,5,6,7,9,10,10aβ-decahydro-7-oxoΔ$^{2(1H),}$ α-phenanthreneacetate [I; R is $C_2H_5$, R°, R' and R'' are H, X is $H_2$, Z is O=C, Δ$^8$], from 3,4,4aα,4bβ,5,6,7,9,10,10aβ-decahydro-7-oxo-2(1H)-phenanthrone (Example 18) and trimethyl phosphonoacetate.

EXAMPLE 40:

Methyl 3,4,4aα,4bβ,5,6,7,8,8aα,9,10,10aβ-dodecahydro-7,7-ethylenedimercapto-Δ$^{2(1H),}$ α-phenanthreneacetate [I; R is $CH_3$, R°, R' and R'' are H, X is $H_2$, Z is ethylenedithio], from 3,4,4aα,4bβ,5,6,7,8-,8aα,9,10,10aβ-dodecahydro-7,7-ethylenedimercapto-2(1H)-phenanthrone (Example 21) and trimethyl phosphono-acetate.

EXAMPLE 41:

Methyl 3,4,4aα,4b ,5,6,7,8,8aα,9,10,10aβ-dodecahydro-4bβ-methyl-7β-hydroxy-Δ$^{2(1H),}$ α-phenanthreneacetate [I; R is $CH_3$, R° is H, R' is $CH_3$, R'' is H, X is $H_2$, Z is (β-HO)CH], from 3,4,4aα,4b,5,6,7,8,8aα,9,10,10aβ-dodecahydro-7β-hydroxy-4bβ-methyl-2(1H)-phenanthrone (Example 22) and trimethyl phosphonoacetate.

EXAMPLE 42:

Methyl 3,4,4aα,4b,5,6,7,8,8aα,9,10,10aβ-dodecahydro-4bβ-methyl-7-oxoΔ$^{2(1H)}$ α-phenanthreneacetate [I; R is CH$_3$, R° is H, R' is CH$_3$, R'' is H, X is H$_2$, Z is O=C], by oxidation of methyl 3,4,4aα,4b,5,6,7,8,-,8aα,9,10,10aβ-dodecahydro-4bβ-methyl-7β-hydroxy-Δ$^{2(1H)}$ α-phenanthreneacetate (Example 41).

EXAMPLE 43:

Ethyl 3,4,4aα,4b,5,6,7,8,8aα,9,10,10aβ-dodecahydro-4bβ-methyl-7β-hydroxy-Δ$^{2(1H)}$ α-phenanthreneacetate [I; R is C$_2$H$_5$, R° is H, R' is CH$_3$, R'' is H, X is H$_2$, Z is (β-HO)CH], from 3,4,4aα,4b,5,6,7,8,-,8aα,9,10,10aβ-dodecahydro-7β-hydroxy-4bβ-methyl-2(1H)-phenanthrone (Example 22) and triethyl phosphono-acetate.

EXAMPLE 44:

Ethyl 3,4,4aα,4b,5,6,7,8,8aα,9,10,10aβ-dodecahydro-4bβ-methyl-7-oxo-Δ$^{2(1H)}$ α-phenanthreneacetate [I; R is C$_2$H$_5$, R° is H, R' is CH$_3$, R'' is H, X is H$_2$, Z is O=C], by oxidation of ethyl 3,4,4aα,4b,5,6,7,8,-,8aα,9,10,10aβ-dodecahydro-4bβ-methyl-7β-hydroxy-Δ$^{2(1H)}$ α-phenanthreneacetate (Example 43).

EXAMPLE 45:

Ethyl 3,4,4aα,4bβ,5,6,7,8,8aβ,9,10,10aβ-dodecahydro-7α-hydroxy-Δ$^{2(1H)}$ α-phenanthreneacetate [I; R is C$_2$H$_5$, R°, R' and R'' are H, X is H$_2$, Z is (α-HO)CH, A/B cis], from 3,4,4aα,4bβ,5,6,7,8,8aβ,9,10,10aα-dodecahydro-7β-hydroxy-2(1H)-phenanthrone (Example 15) and triethyl phosphonoacetate.

EXAMPLE 46:

Ethyl 3,4,4aα,4bβ,5,6,7,8,8aβ,9,10,10aβ-dodecahydro-7-oxo-Δ$^{2(1H)}$ α-phenanthreneacetate [I; R is C$_2$H$_5$, R°, R' and R'' are H, X is H$_2$, Z is O=C, A/B cis], by oxidation of ethyl 3,4,4aα,4bβ,5,6,7,8,8aβ,9,10,10aβ-dodecahydro-7α-hydroxy-Δ$^{2(1H)}$ α-phenanthreneacetate (Example 45).

EXAMPLE 47:

Methyl 3,4,4aα,4bβ,5,6,7,8,aα,910,10aα-dodecahydro-7β-hydroxy-Δ$^{2(1H)}$ α-phenanthreneacetate [I; R is CH$_3$, R°, R' and R'' are H, X is H$_2$, Z is (β-HO)CH, B/C cis], from 3,4,4aα,4bβ,5,6,7,8,8aα,9,10,10aα-dodecahydro-7β-hydroxy-2(1H)-phenanthrone (Example 12) and trimethyl phosphonoacetate.

EXAMPLE 48:

Methyl 3,4,4aα,4b,5,6,7,9,10,10aβ-decahydro-4β-hydroxy-7-oxo-Δ$^{2(1H),α}$-phenanthreneacetate [I; R is CH$_3$, R° is H, R' is OH, R'' is H, X is H$_2$, Z is O=C, Δ$^8$], m.p. 162°–196° C. (from ether), from 1,2,3,4,4aα,4b,5,6,7,9,10,10aβ-dodecahydro-4bβ-hydroxyphenanthrene-2,7-dione (Example 27) and trimethyl phosphonoacetate.

EXAMPLE 49:

Methyl 3,4,4aα,4bβ,5,6,7,8,8aα,9,10,10aβ-dodecahydro-7β-hydroxy-10-oxo-Δ$^{2(1H)}$ α-phenanthreneacetate 7β-acetate [I; R is CH$_3$, R°, R' and R'' are H, X is O, Z is (β-CH$_3$COO)CH], Isomer A, m.p. 131°–133° C. (from ether), and Isomer B, m.p. 145°–149° C. (from ether); from 1,2,3,4,4aα,4bβ,5,6,7,8,8aα,9,10,10aβ-tetradecahydro-7β-acetoxyphenanthrene-2,10-dione (Example 26) and trimethyl phosphonacetate.

EXAMPLE 50:

Ethyl 3,4,4aα,9,10,10aβ-hexahydro-7-methoxy-Δ$^{2(1H)}$ α-phenanthreneacetate [II; R is C$_2$H$_5$, R° is H, R''' is CH$_3$], from 3,4,4aα,9,10,10aβ-hexahydro-7-methoxy-2(1H)-phenanthrone (Example 7) and triethyl phosphonoacetate.

EXAMPLE 51:

Methyl 8,8-dimethyl-7,10-dioxo-3,4,4aα,4bβ,5,6,7,-8,10,10aβ-decahydro-Δ$^{2(1H)}$ α-phenanthreneacetate [I; R is CH$_3$, R°, R' and R'' are H, X is O, Z is O=C, 8,8-(CH$_3$)$_2$, Δ$^{8a,9}$], Isomer A, m.p. 142°–143° C. (from ether); and Isomer B, m.p. 123°–124° C. (from ether), from 3,4,4aα,4bβ,5,6,7,8,10,10aβ-decahydro-8,8-dimethyl-7,10-dioxo-2(1H)-phenanthrone and trimethyl phosphonoacetate.

EXAMPLE 51A:

Ethyl 3,4,4aα,4b,5,6,7,8,8aα,9,10,10aβ-dodecahydro-4bβ-methyl-7β-hydroxy-Δ$^{2(1H)}$ α-phenanthrenepropionate [I; R is C$_2$H$_5$, R° and R' are CH$_3$, R'' is H, X is H$_2$, Z is (β-HO)CH], from 3,4,4aα,4b,5,6,7,8,-,8aα,9,10,10aβ-dodecahydro-4bβ-methyl-7β-hydroxy-2(1H)-phenanthrone and triethyl α-phosphonopropionate.

EXAMPLE 51B:

Methyl 3,4,4aα,5,6,7,8,8aα,9,10,10aβ-dodecahydro-4bβ,8,8-trimethyl-7β-hydroxy-Δ$^{2(1H)}$ α-phenanthreneacetate [I; R is CH$_3$, R° is H, R' is CH$_3$, R'' is H, X is H$_2$, Z is (β-HO)CH, 8,8-(CH$_3$)$_2$], from 3,4,4aα,4b,5,6,7,8,8aα,9,10,10aβ-dodecahydro-4bβ,8,8-trimethyl-7β-hydroxy-a(1H)-phenanthrone and trimethyl phosphonoacetate.

According to the procedures of Examples 32 and 33, the following compounds can be reacted with trimethyl phosphonoacetate:

3,4,4aα,9,10,10aα-Hexahydro-7-methoxy-2(1H)-phenanthrone (Example 4), 3,4,4aα,4bβ,5,6,7,8,8aα,9,10,10aβ-Dodecahydro-7-methyl-7-hydroxy-2(1H)-phenanthrone, 3,4,4aα,4bβ,5,6,7,8,8aα,9,10,10aβ-Dodecahydro-7α-methoxy-2(1H)-phenanthrone, 3,4,4aα,4bβ,5,6,7,8,8aα,9,10,10aβ-Dodecahydro-7β-fluoro-2(1H)-phenanthrone, 3,4,4aα,4bβ,5,6,7,8,8aα,9,10,10aβ-Dodecahydro-7β-chloro-2(1H)-phenanthrone, 3,4,4aα,4bβ,5,6,7,8,8aα,9,10,10aβ-Dodecahydro-7β-bromo-2(1H)-phenanthrone, 3,4,4aα,4b,5,6,7,8,10,10aβ-Decahydro-4bβ,8,8-trimethyl-7-oxo-2(1H)-phenanthrone, and 10-Acetoxy-8,8-dimethyl-3,4,4aα,4bβ,5,6,7,8,10,10aβ-decahydro-7-oxo-2(1H)-phenanthrone to give, respectively, Methyl 3,4,4aα,9,10,10aα-hexahydro-7-methoxy-$\Delta^{2(1H)}$-α-phenanthreneacetate [II; R is $CH_3$, R° is H, R''' is $CH_3$], Methyl 3,4,4aα,4bβ,5,6,7,8,8aα,9,10,10aβ-dodecahydro-7-methyl-7-hydroxy-$\Delta^{2(1H)}$-α-phenanthreneacetate [I; R is $CH_3$, R°, R' and R'' are H, X is $H_2$, Z is $(HO)(CH_3)C$], Methyl 3,4,4aα,4bβ,5,6,7,8,8aα,9,10,10aβ-dodecahydro-7α-methoxy-$\Delta^{2(1H)}$-α-phenanthreneacetate [I; R is $CH_3$, R°, R' and R'' are H, X is $H_2$, Z is (α-$CH_3$O)CH], Methyl 3,4,4aα,4bβ,5,6,7,8,8aα,9,10,10aβ-dodecahydro-7β-fluoro-$\Delta^{2(1H)}$-α-phenanthreneacetate [I; R is $CH_3$, R°, R' and R'' are H, X is $H_2$, Z is (β-F)CH], Methyl 3,4,4aα,4bβ,5,6,7,8,8aα,9,10,10aβ-dodecahydro-7β-chloro-$\Delta^{2(1H)}$-α-phenanthreneacetate [I: R is $CH_3$, R°, R' and R'' are H, X is $H_2$, Z is (β-Cl)CH], Methyl 3,4,4aα,4bβ,5,6,7,8,8aα,9,10,10aβ-dodecahydro-7β-bromo-$\Delta^{2(1H)}$-α-phenanthreneacetate [I; R is $CH_3$, R°, R' and R'' are H, X is $H_2$, Z is (β-Br)CH], Methyl 3,4,4aα,4b,5,6,7,8,10,10aβ-decahydro-4bβ,8,8-trimethyl-7-oxo-$\Delta^{2(1H)}$-α-phenanthreneacetate [I: R is $CH_3$, R° is H, R' is $CH_3$, R'' is H, X is $H_2$, Z is O=C, $\Delta^{8a,9}$], and Methyl 10-acetoxy-8,8-dimethyl-3,4,4aα,4bβ,5,6,7,8,10,10aβ-decahydro-7-oxo-$\Delta^{2(1H)}$-α-phenanthreneacetate [I; R is $CH_3$, R°, R' and R'' are H, X is ($CH_3COO$)(H), Z is O=C, $\Delta^{8a,9}$].

Ethyl 3,4,4aα,4bβ,5,6,7,8,8aα,9,10,10aβ-dodecaahydro-7β-hydroxy-$\Delta^{2(1H)}$-α-phenanthreneacetate (Example 32) can be caused to react with phenyl isocyanate in boiling acetonitrile to give ethyl 3,4,4aα,4bβ,5,6,7,8,8aα,9,10,10aβ-dodecahydro-7β-(N-phenylcarbamoyloxy)-$\Delta^{2(1H)}$-α-phenanthreneacetate [I; R is $CH_3$, R°, R' and R'' are H, X is $H_2$, Z is (p-$C_6H_5$NHCOO)CH].

EXAMPLE 52

3,4,4aα,4bβ,5,6,7,8,8aα,9,10,10aβ-Dodecahydro-7-oxo-$\Delta^{2(1H)}$-α-phenanthreneacetic acid (Isomer A)

[I; R, R°, R' and R'' and H, X is $H_2$, Z is O=C].

A solution of 6.0 g (0.021 mole) of ethyl 3,4,4aα,4bβ,5,6,7,8,8aα,9,10,10aβ-dodecahydro-7-oxo-$\Delta^{2(1H),\alpha}$ phenanthreneacetate (Isomer A) (Example 34a) in 200 ml. of 95% ethanol was treated with 80 ml. (0.16 mole) of 2N aqueous sodium hydroxide and the solution was refluxed for 75 minutes under nitrogen. The reaction mixture was cooled, acidified with acetic acid and concentrated under reduced pressure until the ethanol was removed. The product was extracted from the resulting mixture with ether and then extracted from the ether with 2N aqueous sodium hydroxide. Acidification of this extract with concentrated hydrochloric acid precipitated the product which was collected and recrystallized from ethyl acetate to give 4.2 g. of 3,4,4aα,4bβ,5,6,7,8,8aα,9,10,10aβ-dodecahydro-7-oxo-$\Delta^{2(1H)}$-α-phenanthreneacetic acid (Isomer A), m.p. 224°–227° C. (vac.).

EXAMPLE 53

1,2,3,4,4aα,4bβ,5,6,7,8,8aα,9,10,10aβ-Tetradecanydro-7β-hydroxy-2-phenanthreneacetic (Isomer A)

[I; R, R°, R' and R'' are H, X is $H_2$, Z is (β-HO)CH, saturated side chain].

The ester of Example 35 (4.5 g.) was hydrolyzed according to the procedure of Example 52 and the product was recrystallized once from ethyl acetate to give 3.95 g. (97%) of 1,2,3,4,4aα,4bβ,5,6,7,8,8aα,9,10,10aβ-tetradecahydro-7β-hydroxy-2-phenanthreneacetic acid (Isomer A), m.p. 214°–216° C.

1,2,3,4,4aα,4bβ,5,6,7,8,8aα,9,10,10aβ-Tetradecahydro-7β-hydroxy-2-phenanthreneacetic acid (Isomer B).

The mother liquor residues from Example 35 were hydrolyzed according to the procedure of Example 52. Two recrystallizations of the product from ethyl acetate and one from acetone afforded 3.13 g. of 1,2,3,4,4aα,4bβ,5,6,7,8,8aα,9,10,10aβ-tetradecahydro-7β-hydroxy-2-phenanthreneacetic acid (Isomer B), m.p. 164°–166° C.

By the foregoing hydrolysis procedure the following examples of acids (R is H) were prepared from the corresponding lower-alkyl esters:

EXAMPLE 54:

3,4,4aα,9,10,10aβ-Hexahydro-7-methoxy-$\Delta^{2(1H)}$-α-phenanthreneacetic acid [II; R and R° are H, R''' is $CH_3$], m.p. 174°–175° C. (from acetone-hexane).

EXAMPLE 55:

3,4,4aα,4b,5,6,7,8,8aα,9,10,10aβ-Dodecahydro-4bβ-methyl-$\Delta^{2(1H)}$-α-phenanthreneacetic acid [I; R and R° are H, R' is $CH_3$, R'' is H, X is $H_2$, Z is $CH_2$], m.p. 169°–179° C. (from ethyl acetate).

EXAMPLE 56:

3,4,4aα,4bβ,5,6,7,8,8aα,9,10,10aβ-Dodecahydro-7-oxo-$\Delta^{2(1H)}$-α-phenanthreneacetic acid (Isomer B) [I; R, R°, R' and R'' are H, X is $H_2$, Z is O=C], m.p. 220°–222° C. (vac.) (from ethyl acetate).

EXAMPLE 57:

3,4,4aα,4bβ,5,6,7,8,8aα,9,10,10aβ-Dodecahydro-7α-hydroxy-$\Delta^{2(1H)}$-α-phenanthreneacetic acid [I; R, R°, R' and R'' are H, X is $H_2$, Z is (α-HO)CH], m.p. 173°–189° C. (from ethyl acetate).

EXAMPLE 58:

3,4,4aα,4bβ,5,6,7,8,8aα,9,10,10aβ-Dodecahydro-7β-hydroxy-$\Delta^{1(1H)}$-α-phenanthreneacetic acid [I; R, R°, R' and R'' are H, X is $H_2$, Z is (β-HO)CH], m.p. 205°–207° C. (from ethyl acetate).

EXAMPLE 59:

3,4,4aα,4bβ,3,5,6,7,9,10,10aβ-Decahydro-7-oxo-$\Delta^{2(1H)}$-α-phenanthreneacetic acid [I; R, R°, R' and R'' are H, X is $H_2$, Z is O=C, $\Delta^8$], m.p. 194°–200° C. (from ethyl acetate).

EXAMPLE 60:

3,4,4aα,4bβ,5,6,7,8,8aα,9,10,10aβ-Dodecahydro-7,7-ethylenedimercapto-$\Delta^{2(1H)}$-α-phenanthreneacetic acid [I; R, R°, R' and R'' are H, X is $H_2$, Z is ethylenedithio], m.p. 187°–220° C. (from acetone).

EXAMPLE 61:

3,4,4aα,4b,5,6,7,8,8aα,9,10,10aβ-Dodecahydro-4bβ-methyl-7-oxo-$\Delta^{2(1H)}$, α-phenanthreneacetic acid [I; R and R° are H, R' is CH$_3$, R'' is H, X is H$_2$, Z is O=C], Isomer A, m.p. 181°–184° C. (from ethyl acetate); and Isomer B, m.p. 219°–221° C. (from ethyl acetate).

EXAMPLE 62:

3,4,4aα,4b,5,6,7,8,8aα,9,10,10aβ-Dodecahydro-4bβ-methyl-7β-hydroxy-$\Delta^{2(1H)}$, α-phenanthreneacetic acid [I; R and R° are H, R' is CH$_3$, R'' is H, X is H$_2$, Z is (β-HO)CH], Isomer A, m.p. 223°–225° C; and Isomer B, m.p. 198°–200° C. (from ether).

EXAMPLE 63:

3,4,4aα,4b,5,6,7,8,8aα,9,10,10aβ-Dodecahydro-1β,4bβ-dimethyl-7β-hydroxy-$\Delta^{2(1H)}$, α-phenanthreneacetic acid [I; R and R° are H, R' and R'' are CH$_3$, X is H$_2$, Z is (β-HO)CH].

EXAMPLE 64:

3,4,4aα,4bβ,5,6,7,8,8aβ,9,10,10aβ-Dodecahydro-7-oxo-$\Delta^{2(1H)}$, α-phenanthreneacetic acid [I; R, R°, R' and R'' are H, X is H$_2$, Z is O=C, A/B cis], m.p. 185°–200° C. (from ethyl acetate).

EXAMPLE 65:

3,4,4aα,4bβ,5,6,7,8,8aα,9,10,10aα-Dodecahydro-7β-hydroxy-$\Delta^{2(1H)}$, α-phenanthreneacetic acid [I; R, R°, R' and R'' are H, X is H$_2$, Z is (β-HO)CH, B/C cis].

EXAMPLE 66:

3,4,4aα,4b,5,6,7,9,10,10aβ-Decahydro-4bβ-hydroxy-7-oxo-$\Delta^{2(1H)}$, α-phenanthreneacetic acid [I, R and R° are H, R' is OH, R'' is H, X is H$_2$, Z is O=C, $\Delta^8$], m.p. 208°–232° C. (from acetone).

EXAMPLE 67:

3,4,4aα,4bβ,5,6,7,8,8aα,9,10,10aβ-Dodecahydro-7β-hydroxy-10-oxo-$\Delta^{2(1H)}$, α-phenanthreneacetic acid [I; R, R°, R' and R'' are H, X is O, Z is (β-HO)CH], Isomer A, m.p. 237°–238° C. (from acetone); and Isomer B, m.p. 282°–283° C. (vac.) (from acetone).

EXAMPLE 67A:

3,4,4aα,4b,5,6,7,8,8aα,9,10,10aβ-Dodecahydro-4bβ-methyl-7β-hydroxy-$\Delta^{2(1H)}$, α-phenanthrenepropionic acid [I; R is H, R° and R' are CH$_3$, R'' is H, X is H$_2$, Z is (β-HO)CH].

EXAMPLE 67B:

3,4,4aα,4b,5,6,7,8,8aα,9,10,10aβ-Dodecahydro-4bβ,8,8-trimethyl-7β-hydroxy-$\Delta^{2(1H)}$, α-phenanthreneacetic acid [I; R and R° are H, R' is CH$_3$, R'' is H, X is H$_2$, Z is (β-HO)CH, 8,8-(CH$_3$)$_2$], m.p. 186°–190° C. (from acetone).

According to the procedure of Example 52 the following acids can be prepared by hydrolysis of the corresponding lower-alkyl esters:

3,4,4aα,9,10,10aα-Hexahydro-7-methoxy-$\Delta^{2(1H)}$, α-phenanthreneacetic acid [II; R and R° are H, R''' is CH$_3$],
3,4,4aα,4bβ,5,6,7,8,8aα,9,10,10aβ-Dodecahydro-7-methyl-7-hydroxy-$\Delta^{2(1H)}$, α-phenanthreneacetic acid [I; R, R°, R' and R'' are H, X is H$_2$, Z is (HO)(CH$_3$)C],
3,4,4aα,4bβ,5,6,7,8,8aα,9,10,10aβ-Dodecahydro-7α-methoxy-$\Delta^{2(1H)}$, α-phenanthreneacetic acid [I; R, R°, R' and R'' are H, X is H$_2$, Z is (α-CH$_3$O)CH],
3,4,4aα,4bβ,5,6,7,8,8aα,9,10,10aβ-Dodecahydro-7β-fluoro-$\Delta^{2(1H)}$, α-phenanthreneacetic acid [I; R, R°, R' and R'' are H, X is H$_2$, Z is (β-F)CH],
3,4,4aα,4bβ,5,6,7,8,8aα,9,10,10aβ-Dodecahydro-7β-chloro-$\Delta^{2(1H)}$, α-phenanthreneacetic acid [I; R, R°, R' and R'' are H, X is H$_2$, Z is (β-CL)CH],
3,4,4aα,4bβ,5,6,7,8,8aα,9,10,10aβ-Dodecahydro-7β-bromo-$\Delta^{2(1H)}$, α-phenanthreneacetic acid [I; R, R°, R' and R'' are H, X is H$_2$, Z is (β-Br)CH],
3,4,4aα,4b,5,6,7,8,10,10aβ-Decahydro-4bβ,8,8-trimethyl-7-oxo-$\Delta^{2(1H)}$, α-phenanthreneacetic acid [I; R and R° are H, R' is CH$_3$, R'' is H, X is H$_2$, Z is O=C, $\Delta^{8a,9}$],
3,4,4aα,4bβ,5,6,7,8,10,10aβ-Decahydro-7-oxo-10-hydroxy-$\Delta^{2(1H)}$, α-phenanthreneacetic acid [I; R, R°, R' and R'' are H, X is (H)(OH), Z is O=C, $\Delta^{8a,9}$], and
3,4,4aα,4bβ,5,6,7,8,8aα,9,10,10aβ-Dodecahydro-7β-(N-phenylcarbamoyloxy)-$\Delta^{2(1H)}$, α-phenanthreneacetic acid [I; R, R°, R' and R'' are H, X is H$_2$, Z is (β-C$_6$H$_5$NHCOO)CH].

EXAMPLE 68

7,7-Ethylenedimercapto-3,4,4aα,4b,5,6,7,8,8aα,9,10,10aβ-dodecahydro-4bβ-methyl-$\Delta^{2(1H)}$, α-phenanthreneacetic acid

[I; R and R°are H, R' is CH$_3$, R'' is H, X is H$_2$, Z is (ethylenedithio)C].

A solution of 1.64 g. (5.9 mmoles) of 3,4,4aα,4b,5,6,7,8,9aα,9,10,10aβ-dodecahydro-4bβ-methyl-7-oxo-$\Delta^{2(1H)}$, α-phenanthreneacetic acid (Example 61) in 15 ml. of acetic acid was treated with 2.0 ml. of ethanedithiol followed by 2.0 ml. of boron trifluoride etherate. No heat was evolved but a crystalline precipitate formed immediately. After 5 minutes the mixture was diluted with 15 ml. of water and filtered. The filter cake was washed well with water, air-dried and recrystallized from 100 ml. of acetic acid to give 1.56 g. of 7,7-ethylenedimercapto-3,4,4aα,4b,5,6,7,8,8aα,9,10,-10aβ-dodecahydro-4bβ-methyl-$\Delta^{2(1H)}$, α-phenanthreneacetic acid, m.p. 254°–259° C.

By replacing the ethanedithiol in the foregoing preparation by a molar equivalent amount of ethylene glycol, 1,3-propylene glycol, or 1,3-propanedithiol, there can be obtained, respectively, 7,7-ethylenedioxy-3,4,4aα,4b,5,6,7,8,8aα,9,10,10aβ-dodecahydro-4bβ-methyl-$\Delta^{2(1H)}$, α-phenanthreneacetic acid [I; R and R° are H, R' is CH$_3$, R'' is H, X is H$_2$, Z is (ethylenedioxy)C], 7,7-(1,3-propylenedioxy)-3,4,4aα,4b,5,6,7,8,8aα,9.10,10aβ-dodecahydro-4bβ-methyl-$\Delta^{2(1H)}$, α-phenanthreneacetic acid [I; R and R° are H, R' is CH$_3$, R'' is H, X is H$_2$, Z is (1,3-propylenedioxy)C], or 7,7-(1,3-propylenedimercapto)-3,4,4aα,4b,-5,6,7,8,8aα,9,10,10aβ-dodecahydro-4bβ-methyl-$\Delta^{2(1H)}$, α-phenanthreneacetic acid [I; R and R° are H, R' is CH$_3$, R'' is H, X is H$_2$, Z is (1,3-propylenedithio)C].

Similarly, 3,4,4aα,4b,5,6,7,8,8aα,9,10,10aβ-dodecahydro-4bβ-methyl-7-oxo-$\Delta^{2(1H),\alpha}$-phenanthreneacetic acid was caused to react with benzylmercaptan to give 7,7-dibenzylmercapto-3,4,4aα,4b,5,6,7,8,8aα,9,10,10aβ-dodecahydro-4bβ-methyl-$\Delta^{2(1H)}$, α-phenanthreneacetic acid [I; R and R° are H, R' is CH$_3$, R" is H, X is H$_2$, Z is (C$_6$H$_5$CH$_2$S)$_2$C], m.p. 187°–194° C.

EXAMPLE 69

7,7-ethylenedisulfonyl)-3,4,4a$\alpha$,4b$\beta$,5,6,7,8,8a$\alpha$,9,10,-10a$\beta$-dodecahydro-$\Delta^{2(1H)}$, $\alpha$-phenanthreneacetic acid [I; R, R°, R' and R" are H, X is H$_2$, Z is (ethylenedisulfonyl)C].

A solution of 1.2 g. (3.5 mmoles) of 7,7-(ethylenedimercapto)-3,4,4a$\alpha$,4b$\beta$,5,6,7,8,8a$\alpha$,9,10,-10a$\beta$-dodecahydro-$\Delta^{2(1H)}$, $\alpha$-phenanthreneacetic acid (Example 60) in 150 ml. of ether was treated with 3.08 g. (17 mmoles) of monoperphthalic acid in 21 ml. of ether. The solution was kept overnight at room temperature, 150 ml. of tetrahydrofuran was added and the solution was left for three more days. Ether (500 ml.) was added and the solution was washed with saturated sodium sulfite solution and brine and then dried over sodium sulfate. The solution was concentrated to give a crystalline residue which was triturated with about 20 ml. of chloroform and collected on a filter; 1.13 g., m.p. 266°–267° C. (dec.). A second crop of 0.19 g., m.p. 267°–270° C., was obtained by concentration of the chloroform washings (92% yield). Recrystallization from acetone gave 7,7-(ethylenedisulfonyl)-3,4,4a$\alpha$,4b$\beta$,5,6,7,8,8a$\alpha$,9,10,10a$\beta$-dodecahydro-$\Delta^{2(1H)}$, $\alpha$-phenanthreneacetic acid, m.p. 270°–271° C.

Similarly, 7,7-dibenzylmercapto-3,4,4a$\alpha$,4b,5,6,7,8-,8a$\alpha$-9,10,10a$\beta$-dodecahydro-4b$\beta$-methyl-$\Delta^{2(1H)}$, $\alpha$-phenanthreneacetic acid was oxidized to 7,7-dibenzylsulfonyl-3,4,4a$\alpha$,4b,5,6,7,8,8a$\alpha$,9,10,10a$\beta$-dodecahydro-4b$\beta$-methyl-$\Delta^{(1H)}$, $\alpha$-phenanthreneacetic acid [I; R and R° are H, R' is CH$_3$, R" is H, X is H$_2$, Z is (C$_6$H$_5$CH$_2$SO$_2$)$_2$C], m.p. 152°–154° C.

EXAMPLE 70

3,4,4a$\alpha$,4b,5,6,7,8,8a$\alpha$,9,10,10a$\beta$-Dodecahydro-4b$\beta$-methyl-7$\beta$-pyrrolidino-$\Delta^{2(1H)}$, $\alpha$-phenanthreneacetic acid

[I; R and R° are H, R' is CH$_3$, R" is H, X is H$_2$, Z is (CH$_2$)$_4$NCH].

A mixture of 3.10 g. (11.2 mmoles) of 3,4,4a$\alpha$,4b,5,6,7,8,8a$\alpha$,9,10,10a$\beta$-dodecahydro-4b$\beta$-methyl-7oxo-$\Delta^{2(1H)}$, $\alpha$-phenanthreneacetic acid (Example 61), 75 ml. of benzene and 8 ml. (96 mmoles) of pyrrolidine was heated under reflux for 4½ hours with a water separator attached to the system. This solution was concentrated to a residue by warming under reduced pressure and the residue was treated with 50 ml. of dry benzene and 3.5 ml. (93 mmoles) of formic acid. The mixture was heated under reflux for 30 minutes, cooled and treated with 1.5 ml. of formic acid. Water (60 ml.) and ether (100 ml.) were added and the layers were separated. The ether layer was extracted once with 2N hydrochloric acid and discarded. Addition of the acidic extract to the aqueous portion of the reaction mixture caused precipitation of the hydrochloride salt of the product. Concentrated hydrochloric acid (3 ml.) and 10 ml. of brine were added and the precipitate was collected. It was washed well with acetonitrile and then ether to give 2.57 g. of 3,4,4a$\alpha$,4b,5,6,7,8-,8a$\alpha$,9,10,10a$\beta$-dodecahydro-4b$\beta$-methyl-7$\beta$-pyrrolidino-$\Delta^{2(1H)}$, $\alpha$-phenanthreneacetic acid which was suitable for conversion to a basic ester.

By replacing the pyrrolidine in the foregoing preparation by a molar equivalent amount of diethylamine or piperidine there can be obtained, respectively, 3,4,4a$\alpha$,4b,5,6,7,8,8a$\alpha$,9,10, 10a$\beta$-dodecahydro-4b$\beta$-methyl-7$\beta$-diethylamino-$\Delta^{2(1H)}$, $\alpha$-phenanthreneacetic acid [I; R and R° are H, R' is CH$_3$, R" is H, X is H$_2$, Z is (C$_2$H$_5$)$_2$N CH], or 3,4,4a$\alpha$,4b,5,6,7,8,8a$\alpha$,9,10,10a$\beta$-dodecahydro-4b$\beta$-methyl-7$\beta$-piperidino-$\Delta^{2(1H)}$, $\alpha$-phenanthreneacetic acid [I; R and R° are H, R' is CH$_3$, R" is H, X is H$_2$, Z is (CH$_2$)$_5$NCH].

EXAMPLE 71

8,8-Dimethyl-7,10-dioxo-3,4,4a$\alpha$, 4b$\beta$,5,6,7,8,10,10a$\beta$-decahydro-$\Delta^{2(1H)}$, $\alpha$-phenanthreneacetic acid

[I; R, R°, R' and R" are H, X is O, Z is O=C, 8,8-(CH$_3$)$_2$, $\Delta^{8a,9}$]can be prepared from the corresponding methyl ester (Example 51) by methods which do not open Ring A, for example, by heating the methyl ester with anhydrous lithium iodide in the presence of a suitable solvent such as collidine.

Conventional aqueous alkaline hydrolysis of the methyl ester leads to a compound where Ring A has been opened as follows:

Methyl 8,8-dimethyl-3,4,4a$\alpha$,4b$\beta$,5,6,7,8,10,10a$\beta$-decahydro-7,10-dioxo-$\Delta^{2(1H)}$, $\alpha$-phenanthreneacetate (Isomer A) (Example 51) (810 mg., 2.5 millimoles) in 20 ml. of ethanol and 8 ml. of 2N sodium hydroxide was boiled under reflux in a nitrogen atmosphere for 1 hour. The reaction mixture was added to ice-water and was made acidic with dilute hydrochloric acid. Sodium chloride was added to the reaction mixture which was then extracted with ether. The ether was dried (Na$_2$SO$_4$) and evaporated to afford 810 mg. of residue. The residue was chromatographed on 100 g. of silica gel. Elution with acetic acid-ether-pentane (3:50:47) afforded 230 mg. of 5$\alpha$-(2-carboxethyl)-3,4,4a$\alpha$,5,8,8a$\beta$-hexahydro-6-isopropyl-8-oxo-$\Delta^{2(1H)}$, $\alpha$-naphthaleneacetic acid (Isomer A), m.p. 186°–190° C. Recrystallization from ether gave a sample that melted at 194°–195 C.

Similarly, methyl 8,8-dimethyl-3,4,4a$\alpha$,4b$\beta$,5,6,7,8,10,10a$\beta$-decahydro-7,10-dioxo-$\Delta^{2(1H)}$, $\alpha$-phenanthreneacetate (Isomer B) (Example 51) was hydrolyzed to 5$\alpha$(2-carboxyethyl)-3,4,4a$\alpha$,5,8,8a$\beta$-hexahydro-6-isopropyl-8-oxo-$\Delta^{2(1H),\alpha}$-naphthalenacetic acid (Isomer B), m.p. 213°–215° C. (from ether).

5$\alpha$(2-Carboxyethyl)-3,4,4a$\alpha$,5,8,8a$\beta$-hexahydro-6-isoproply-8-oxo-$\Delta^{2(1H)}$, $\alpha$-naphthaleneacetic acid (Isomers A and B) were found to have antibacterial activity when tested in vitro against conventional test organisms such as *Staph. aureus* and *E. typhi*.

EXAMPLE 72

2-Dimethylaminoethyl 3,4,4a$\alpha$,4b$\beta$,5,6,7,8,8a$\alpha$,9,10,10a$\beta$-dodecahydro-7-oxo-$\Delta^{2(1H)}$, $\alpha$-phenanthreneacetate (Isomer A)

[I; R is CH$_2$CH$_2$N(CH$_3$)$_2$, R°, R' and R" are H, X is H$_2$, Z is O=C].

A solution of 4.47 g. (0.017 mole) of the ·3,4,4a$\alpha$,4b$\beta$,5,6,7,8,8a$\alpha$,9,10,10a$\beta$-dodecahydro-7-oxo-$\Delta^{2(1H)}$, $\alpha$-phenanthreneacetic acid (Isomer A) (Example 52) in 100 ml. of tetrahydrofuran was treated with 0.92 g (0.17 mole) of sodium methoxide and 1 ml. of water. The solvent was then removed by warming under reduced pressure, 20 ml. of absolute ethanol was added and evaporated in the same manner and, finally, two 20-ml. portions of dry benzene were added and evaporated. The resulting dry sodium salt was suspended in 150 ml. of dry benzene, 3.46 g. (0.044 mole) of pyridine was added, the mixture was immersed in an ice bath and 40 ml. of oxalyl chloride was added in a fast stream of drops with stirring. The mixture was removed from the ice bath, stirred for 10 minutes and then concentrated as rapidly as possible under reduced pressure using a water bath at 45° C. Application of heat was stopped as the last of the solvent evaporated, and 150 ml. of benzene was added followed by 40 ml. of 2-dimethylaminoethanol in a rapid stream of drops with stirring and cooling. When addition was complete, the mixture was heated on the steam bath for 5 minutes, cooled and diluted with 1 liter of ether and 600 ml. of saturated aqueous sodium carbonate. The layers were separated and the water layer was washed with ether and discarded. The combined ether layers were extracted with two 100-ml. portions and one 50-ml. portion of 2N hydrochloric acid and the combined extracts were made basic with sodium hydroxide solution. This alkaline mixture was extracted with ether and the extracts were washed with brine and dried over sodium sulfate. Removal of the ether afforded 4.9 g. of a yellow oil which was (by glpc) a 96% trans-4% cis mixture of isomers together with 12% of impurity.

The product was purified by partition chromatography. The solvent system employed was a 12:1:2:0.2 mixture of hexane, ethylene dichloride, methanol and water. Infusorial earth (300 g.) was wet with 225 ml. of the polar phase containing 75 mg. of bromcresol purple, the color of the mixture was adjusted to a pale creamy yellow (faintly acid) by gaseous hydrogen chloride and the solid was packed into a column 9 cm. in diameter. The sample was dispersed on 10 g. of infusorial earth and placed on the top of the column. Elution of the column with the non-polar phase of the solvent mixture developed the column; the position of all basic material was clearly revealed by blue bands. The product was recovered either by elution or slicing of the column, depending on the separation of the bands. In the present case the product was eluted to yield 4.39 g. of the basic ester mixture which was free of significant impurities.

The 4.39 g. of oil was dissolved in 200 ml. of ether and treated with 1.11 ml. of concentrated hydrochloric acid in 20 ml. of absolute alcohol. The precipitated hydrochloride salt was collected and recrystallized twice from acetone to give 3.56 g. of 2-dimethylaminoethyl 3,4,4a$\alpha$,4b$\beta$,5,6,7,8,8a$\alpha$,9,10,10a$\beta$-dodecahydro-7-oxo-$\Delta^{2(1H)}$, $\alpha$-phenanthreneacetate (Isomer A) in the form of its hydrochloride salt, colorless plates, m.p. 180°–182.0° C.

Similarly there was prepared 2-dimethylaminoethyl 3,4,4a$\alpha$,4b$\beta$,5,6,7,8,8a$\alpha$,9,10,10a$\beta$-dodecahydro-7-oxo-$\Delta^{2(1H)}$, $\alpha$-phenanthreneacetate Isomer B, hydrochloride salt, m.p. 174.5°–175.5° C. (from acetone) containing ¼ mole of water of crystallization.

By replacing the 2-dimethylaminoethanol in the foregoing preparation by a molar equivalent amount of 2-(1-piperidyl)ethanol, 2-(1-pyrrolidyl)ethanol, 2-(4-morpholinyl)ethanol, 2-(4-methyl-1-piperidyl)ethanol, or 2-(4-methyl-1-piperazinyl)ethanol, there can be obtained, respectively 2-(1-piperidyl)ethyl 3,4,4a$\beta$,5,6,7,8,8a$\alpha$,9,10,10a$\beta$-dodecahydro-7-oxo-$\Delta^{2(1H)}$, $\alpha$-phenanthreneacetate [I; R is $CH_2CH_2N(CH_2)_5$, R°, R' and R'' are H, X is $H_2$, Z is O=C], 2-(1-pyrrolidyl)ethyl 3,4,4a$\alpha$,4b$\beta$,5,6,7,8- ,8a$\alpha$,9,10,10a$\beta$-dodecahydro-7-oxo-$\Delta^{2(1H)}$, $\alpha$-phenanthreneacetate [I; R is $CH_2CH_2N(CH_2)_4$, R°, R' and R'' are H, X is $H_2$, Z is O=C], 2-(4-morpholinyl)ethyl 3,4,4a$\alpha$,4b$\beta$,5,6,7,8,8a$\alpha$,9,10,10a$\beta$-dodecahydro-7-oxo-$\Delta^{2(1H)}$, $\alpha$-phenanthreneacetate [I; R is $CH_2CH_2N(CH_2)_4O$, R°, R' and R'' are H, X is $H_2$, Z is O=C], 2-(4-methyl-1-piperidyl)ethyl 3,4,4a$\alpha$,4b$\beta$,5,6,7,8,8a$\alpha$,9,10,10a$\beta$-dodecahydro-7-oxo-$\Delta^{2(1H)}$, $\alpha$-phenanthreneacetate [I; R is $CH_2CH_2N(CH_2)_4CHCH_3$, R°, R' and R'' are H, X is $H_2$, Z is O=C], or 2-(4-methyl-1-piperazinyl)ethyl 3,4,4a$\alpha$,4b$\beta$,5,6,7,8,8a$\alpha$,9,10,10a$\beta$,-dodecahydro-7-oxo-$\Delta^{2(1H)}$, $\alpha$-phenanthreneacetate [I; R is $CH_2CH_2N(CH_2)_4NCH_3$, R°, R' and R'' are H, X is $H_2$, Z is O=C].

By the foregoing esterification procedure the following examples of basic esters (R is amino-lower-alkyl) were prepared from the corresponding acids (R is H):

EXAMPLE 73:

2-Diethylaminoethyl 3,4,4a$\alpha$,9,10,10a$\beta$-hexahydro-7-methyl-$\Delta^{2(1H)}$, $\alpha$-phenanthreneacetate [II, R is $CH_2CH_2CH_2N(CH_3)_2$, R° is H, R''' is $CH_3$], hydrochloride salt, m.p. 179°–183° C. (from acetone).

EXAMPLE 74:

2-Dimethylaminoethyl 1,2,3,4,4a$\alpha$,4b$\beta$,5,6,7,8- ,8a$\alpha$,9,10,10a$\beta$-tetradecahydro-7$\beta$-hydroxy-2-$\alpha$ phenanthreneacetate [I; R is $CH_2CH_2N(CH_3)_2$, R°, R' and R'' are H, X is $H_2$, Z is ($\beta$-HO)CH, saturated side chain], Isomer A, hydrochloride salt, m.p. 255.0°–256.0° C. (from methanol-ether); and Isomer B, hydrochloride salt, m.p. 199.8°–216.0° C. (from acetone).

EXAMPLE 75:

2-Dimethylaminoethyl 3,4,4a$\alpha$,4b,5,6,7,8,8a$\alpha$,9,10,- 10a$\beta$-dodecahydro-4b$\beta$-methyl-$\Delta^{2(1H)}$, $\alpha$-phenanthreneacetate [I; R is $CH_2CH_2N(CH_3)_2$, R° is H, R' is $CH_3$, R'' is H, X is $H_2$, Z is $CH_2$], hydrochloride salt, m.p. 192°–198° C. (from acetonitrile).

EXAMPLE 76:

2-Dimethylaminoethyl 3,4,4a$\alpha$,4b$\beta$,5,6,7,8- ,8a$\alpha$,9,10,10a$\beta$-dodecahydro-7-oxo-$\Delta^{2(1H)}$, $\alpha$-phenanthreneacetate [I; R is $CH_2CH_2N(CH_3)_2$, R°, R' and R'' are H, X is $H_2$, Z is O=C], hydrochloride salt, m.p. 156°–162° C. (colorless needles from acetone).

EXAMPLE 77:

2-Dimethylaminoethyl 3,4,4a$\alpha$,4b$\beta$,5,6,7,8- ,8a$\alpha$,9,10,10a$\beta$-dodecahydro-7$\alpha$-hydroxy-$\Delta^{2(1H)}$, $\alpha$-phenanthreneacetate [I; R is $CH_2CH_2N(CH_3)_2$, R°, R' and R'' are H, X is $H_2$, Z is ($\alpha$-HO)CH], methanesulfonate salt, m.p. 167°–169° C. (colorless needles from acetone).

EXAMPLE 78:

2-Dimethylaminoethyl 3,4,4a$\alpha$,4b$\beta$,5,6,7,9,10,10a$\beta$-decahydro-7-oxo-$\Delta^{2(1H)}$, $\alpha$-phenanthreneacetate [I; R is $CH_2CH_2N(CH_3)_2$, R°, R' and R'' are H, X is $H_2$, Z is O=C, $\Delta^8$], hydrochloride salt, m.p. 149°–188° C. (from ethyl acetate).

EXAMPLE 79:

2-Dimethylaminoethyl 3,4,4a$\alpha$,4b,5,6,7,8,8a$\alpha$,9,10,- 10a$\beta$-dodecahydro-7,7-ethylenedimercapto-4b$\beta$-methyl-$\Delta^{2(1H)}$, $\alpha$-phenanthreneacetate [I; R is CH₂CH₂N(CH₃)₂, R° is H, R' is CH₃, R'' is H, X is H₂, Z is (ethylenedithio)C], free base, m.p. 116°–120° C. (from acetone); hydrochloride salt, m.p. 230°–232° C. (from methanol-ether-pentane).

EXAMPLE 80:

2-Dimethylaminoethyl 3,4,4aα,4bβ,5,6,7,8-,8aα,9,10,10aβ-dodecahydro-7,7-ethylenedisulfonyl-$\Delta^{2(1H)}$, α-phenanthreneacetate [I; R is CH₂CH₂N(CH₃)₂, R°, R' and R'' are H, Y is H₂, Z is (ethylenedisulfonyl)C], hydrochloride salt, m.p. 255°–260° C. (from acetone).

EXAMPLE 81:

2-Dimethylaminoethyl 3,4,4aα,4b,5,6,7,8,8aα,9,10,-10aβ-dodecahydro-4bβ-methyl-7-oxo-$\Delta^{2(1H)}$, α-phenanthreneacetate [I; R is CH₂CH₂N(CH₃)₂, R° is H, R' is CH₃, R'' is H, X is H₂, Z is C=C], methanesulfonate salt, m.p. 146°–148° C.(dec.) (from ethyl acetate).

EXAMPLE 82:

2-Dimethylaminoethyl 3,4,4aα,4b,5,6,7,8aα,9,10,-10aβ-dodecahydro-4bβ-methyl-7β-pyrrolidino-$\Delta^{2(1H)}$, α-phenanthreneacetate [I; R is CH₂CH₂N(CH₃)₂, R° is H, R' is CH₃, R'' is H, X is H₂, Z is (CH₂)₄NCH], dihydrochloride salt, m.p. 280° C. (dec.), (colorless plates from acetonitrile).

EXAMPLE 83:

3-Dimethylaminopropyl 3,4,4aα,4bβ,5,6,7,8-,8aα,9,10,10aβ-dodecahydro-7-oxo-$\Delta^{2(1H)}$, α-phenanthreneacetate [I; R is CH₂CH₂CH₂N(CH₃)₂, R°, R' and R'' are H, X is H₂, Z is O=C], methanesulfonate salt, m.p. 158°–165° C. (colorless needles from acetone).

EXAMPLE 84:

3-dimethylaminopropyl 3,4,4aα,4bβ,5,6,7,8-,8aα,9,10,10aβ-dodecahydro-7β-hydroxy-$\Delta^{2(1H)}$, α-phenanthreneacetate [I; R is CH₂CH₂CH₂N(CH₃)₂, R°, R' and R'' are H, X is H₂, Z is (β-HO)CH], hydrochloride salt, m.p. 176°–184° C. (from acetone).

EXAMPLE 85:

4-Dimethylaminobutyl 3,4,4aα,4b,5,6,7,8,8aα,9,10,-10aβ-dodecahydro-4bβ-methyl-7-oxo-$\Delta^{2(1H)}$, α-phenanthreneacetate [I; R is (CH₂)₄N(CH₃)₂, R° is H, R' is CH₃, R'' is H, X is H₂, Z is O=C], hydrochloride salt, m.p. 130°–138° C. (from ethyl acetate).

EXAMPLE 86:

2-Diethylamino-1-methylethyl 3,4,4aα,4b,5,6,7,8-,8aα,9,10,10aβ-dodecahydro-4bβ-methyl-7β-hydroxy-$\Delta^{2(1H)}$, α-phenanthreneacetate [I; R is CH(CH₃)CH₂N(CH₃)₂, R° is H, R' is CH₃, R'' is H, X is H₂, Z is (β-HO)CH], methanesulfonate salt, m.p. 202°–208° C. (from acetonitrile).

EXAMPLE 87:

2-Diethylaminoethyl 3,4,4aα,4bβ,5,6,7,8,8aα,9,10,-10aβ-dodecahydro-7-hydroxy-$\Delta^{2(1H)}$, α-phenanthreneacetate [I; R is CH₂CH₂N(C₂H₅)₂, R°, R' and R'' are H, X is H₂, Z is (β-HO)CH], hydrochloride salt, m.p. 147°–155° C. (from acetone-ether).

EXAMPLE 88:

Diisopropylaminoethyl 3,4,4aα,4bβ,5,6,7,8-,8aα,9,10,10aβ-dodecahydro-7β-hydroxy-$\Delta^{2(1H)}$, α-phenanthreneacetate [I; R is CH₂CH₂N[CH(CH₃)₂]₂, R°, R' and R'' are H, X is H₂, Z is (β-HO)CH], hydrochloride salt, m.p. 183°–185° C. (from acetone).

EXAMPLE 89:

1-Methyl-4-piperidyl 3,4,4aα,4bβ,5,6,7,8,8aα,9,10,-10aβ-dodecahydro-7-oxo-$\Delta^{2(1H)}$, α-phenanthreneacetate [I; R is 1-methyl-4-piperidyl, R°, R' and R'' are H, X is H₂, Z is O=C], hydrochloride salt, m.p. 155°–170° C. (dec.) (from ethyl acetate).

EXAMPLE 90:

2-Dimethylaminoethyl 3,4,4aα,4b,5,6,7,8,8aα,9,10,-10aβ-dodecahydro-7β-hydroxy-1β,4bβ-dimethyl-$\Delta^{2(1H)}$, α-phenanthreneacetate [I; R is CH₂CH₂N(CH₃)₂, R° is H, R' and R'' are CH₃, X is H₂, Z is (β-HO)CH], hydrochloride salt, m.p. 238°–242° C. (from acetonitrile).

EXAMPLE 91:

2-Dimethylaminoethyl 3,4,4aα,4bβ,5,6,7,8-,8aβ,9,10,10aβ-dodecahydro-7-oxo-$\Delta^{2(1H)}$, α-phenanthreneacetate [I; R is CH₂CH₂N(CH₃)₂, R°, R' and R'' are H, X is H₂, Z is O=C, A/B cis], hydrochloride salt, m.p. 181°–188° C. (colorless needles from acetone).

EXAMPLE 92:

2-Dimethylaminoethyl 3,4,4aα,4bβ,5,6,7,8-,8aα,9,10,10aα-dodecahydro-7β-hydroxy-$\Delta^{2(1H)}$, α-phenanthreneacetate [I; R is CH₂CH₂N(CH₃)₂, R°, and R'' are H, X is H₂, Z is (β-HO)CH, B/C cis], methanesulfonate salt, m.p. 184°–202° C. (from acetone-ether).

EXAMPLE 93:

3-Dimethylaminopropyl 3,4,4aα,4bβ,5,6,7,8-,8aα,9,10,10aβ-dodecahydro-7,7-ethylenedisulfonyl-$\Delta^{2(1H)}$, α-phenanthreneacetate [I; R is CH₂CH₂CH₂N(CH₃)₂, R°, R' and R'' are H, X is H₂, Z is (ethylenedisulfonyl)C], hydrochloride salt, m.p. 244°–247° C. (from methanol-ether).

EXAMPLE 94:

2-Dimethylaminoethyl 3,4,4aα,4bβ,5,6,7,8-,8aα,9,10,10aβ-dodecahydro-7β-hydroxy-10-oxo-$\Delta^{2(1H)}$, α-phenanthreneacetate [I; R is CH₂CH₂N(CH₃)₂, R°, R' and R'' are H, X is O, Z is (β-HO)CH], Isomer A, hydrochloride salt, m.p. 214°–217° C. (from acetone); Isomer B, hydrochloride salt, m.p. 224°–226° C.

EXAMPLE 95:

2-Dimethylaminoethyl 3,4,4aα,4b,5,6,7,8,8aα,9,10,-10aβ-dodecahydro-7,7-dibenzylsulfonyl-4bβ-methyl-$\Delta^{2(1H)}$, α-phenanthreneacetate [I; R is CH₂CH₂N(CH₃)₂, R° is H, R' is CH₃, R'' is H, X is H₂, Z is (C₆H₅CH₂SO₂)₂C], hydrochloride salt, m.p. 142°–153° C. (from acetone-ether).

EXAMPLE 96

2-Dimethylaminoethyl αβ3,4,4aα,4b,5,6,7,8-,8aα,9,10,10β-dodecahydro-4bβ-methyl-7β-hydroxy-$\Delta^{2(1H)}$, α-phenanthrenepropionate [I; R is CH₂CH₂N(CH₃)₂, R° and R' are CH₃, R'' is H, X is H₂, Z is (β-HO)CH], hydrochloride salt, m.p. 249°–259° C. (from methanol-ether).

EXAMPLE 96A:

2-Dimethylaminoethyl 3,4,4aα,4b,5,6,7,8,8aα,9,10,-10aβ-dodecahydro-4bβ,8,8-trimethyl-7β-hydroxy-$\Delta^{2(1H)}$,$^\alpha$-phenanthreneacetic acid [I; R is $CH_2CH_2N(CH_3)_2$, R° is H, R' is $CH_3$, R'' is H, X is $H_2$, Z is (β-HO)CH, 8,8-$(CH_3)_2$], hydrochloride salt, m.p. 202°–224° C. (from acetone).

EXAMPLE 97

2-Dimethylaminoethyl 3,4,4aα,4b,5,6,7,8,8aα,9,10,-10aβ-dodecahydro-7β-hydroxy-4bβ-methyl-$\Delta^{2(1H)}$,$^\alpha$-phenanthreneacetate [I; R is $CH_2CH_2N(CH_3)$, R° is H, R' is $CH_3$, R'' is H, X is $H_2$, Z is (β-HO)CH].

A 3.65 g. sample (10.5 mmoles) of amorphous 2-dimethylaminoethyl 3,4,4aα,4b,5,6,7,8,8aα,9,10,10aβ-dodecahydro-4bβ-methyl-7-oxo-$\Delta^{2(1H)}$,$^\alpha$-phenanthreneacetate (Example 81) was dissolved in 100 ml. of methanol and stirred while 0.53 g. of sodium borohydride was added in small portions. The solution was allowed to stand overnight at room temperature, acidified with 2N sulfuric acid and concentrated by warming under reduced pressure until the methanol was removed. The aqueous residue was diluted with 250 ml. of water, washed with ether and made alkaline with 2N aqueous sodium hydroxide. The precipitated product was extracted with ether and the extracts were washed with water and brine and dried over magnesium sulfate. Concentration afforded 3.00 g. of colorless, oily 2-dimethylaminoethyl 3,4,4aα,4b,5,6,7,8,8aα,9,10,10aβ-dodecahydro-7β-hydroxy-4bβ-methyl-$\Delta^{2(1H)}$,$^\alpha$-phenanthreneacetate, obtained in the form of its hydrochloride salt, m.p. 218°–236° C. when recrystallized from acetonitrile.

Separation of the Isomers A and B - The amorphous base obtained above (2.3 g., 6.6 mmoles) dissolved in 30 ml. of ethyl acetate was treated with 0.53 g. (5.5 mmoles) of methanesulfonic acid dissolved in 20 ml. of ethyl acetate. The precipitate which formed was collected and recrystallized three times from acetonitrile to give 0.74 g. (25%) of solid, m.p. 232°–236° C. (dec.). One further recrystallization afforded 2-dimethylaminoethyl 3,4,4aα,4b,5,6,7,8,8aα,9,10,10aβ-dodecahydro-7β-hydroxy-4bβ-methyl-$\Delta^{2(1H)}$,$^\alpha$-phenanthreneacetate (Isomer A), in the form of its methanesulfonate salt, m.p. 237.4°–240.6° C. (dec.).

Concentration of each of the three mother liquors separately in the above separation of Isomer A of m.p. 232°–236° C. afforded the more soluble Isomer B in crops of 0.20 g., m.p. 213°–218° C; 0.25 g., m.p. 218°–221° C.; 0.20 g., m.p. 219°–223° C.; total yield 0.65 g. (22%). A single recrystallization from acetonitrile furnished the pure Isomer B, colorless plates, m.p. 215.0°–220.0° C.

EXAMPLE 98

2-Dimethylaminoethyl 3,4,4aα,4bβ,5,6,7,8,8aβ,9,10,10aβ-dodecahydro-7α-hydroxy-$\Delta^{2(1H)}$,$^\alpha$-phenanthreneacetate

[I; R is $CH_2CH_2N(CH_3)_2$, R°, R' and R'' are H, X is $H_2$, Z is (α-HO)CH].

2-Dimethylaminoethyl 3,4,4aα,4bβ,5,6,7,8,8aα,9,10,10aβ-dodecahydro-7-oxo-$\Delta^{2(1H)}$,$^\alpha$-phenanthreneacetate (Example 72) (1.27 g.) was dissolved in 60 ml. of 95% ethanol, 150 mg. of sodium borohydride in 5 ml. of water was added and the mixture was left standing for 1 hour at room temperature. Acetone and dilute hydrochloric acid were added and the ethanol was removed by warming under reduced pressure. Ether was added, the layers were separated and the ether layer was extracted with 2N hydrochloric acid. The combined layers were made alkaline with sodium hydroxide solution and extracted with ether. These extracts were washed with brine, dried ($Na_2SO_4$) and concentrated. The residue was subjected to partition chromatography, converted to its hydrochloride salt and recrystallized from acetone to give 2-dimethylaminoethyl 3,4,4aαα,4bβ,5,6,7,8,8aβ,9,10,10aβ-dodecahydro-7α-hydroxy-$\Delta^{2(1H)}$,$^\alpha$-phenanthreneacetate in the form of its hydrochloride salt, colorless needles, m.p. 196.0°–198.0° C.

EXAMPLE 99

2-Dimethylaminoethyl 3,4,4aα,4b,5,6,7,8,8aα,9,10,10aβ-*dodecahydro*-7β-hydroxy-4bβ-methyl-$\Delta^{2(1H)}$,$^\alpha$-phenanthreneacetate 7-benzoate

[I; R is $CH_2CH_2N(CH_3)_2$, R° is H, R' is $CH_3$, R'' is H, X is $H_2$, Z is ($C_6H_5COO$)CH].

A solution of 0.90 g. of the free base, 2-diethylaminoethyl 3,4,4aα,4b,5,6,7,8,8aα,9,10,10aβ-dodecahydro-7β-hydroxy-4bβ-methyl-$\Delta^{2(1H)}$,$^\alpha$-phenanthreneacetate (Example 97), in 50 ml. of dry benzene was treated with 0.5 ml. of pyridine and 2.0 ml. of benzoyl chloride and heated on the steam bath for 5 minutes. The solvents were removed by warming under reduced pressure and the residue was partitioned between 2N aqueous sodium hydroxide and methylene dichloride. The organic layer was separated, washed with brine, dried ($Na_2SO_4$) and concentrated to give 1.3 g. of a crystalline residue. This base was dissolved in hot acetonitrile, 0.3 ml. of 8N alcoholic hydrogen chloride was added and the mixture cooled to give 2-dimethylaminoethyl 3,4,4aα,4b,5,6,7,8,8aα,9,10,10aβ-dodecahydro-7β-hydroxy-4bβ-methyl-$\Delta^{2(1H)}$,$^\alpha$-phenanthreneacetate 7-benzoate in the form of its hydrochloride salt, m.p. 225.4°–230.0° C. when recrystallized from acetonitrile.

EXAMPLE 100

2-Dimethylaminoethyl 3,4,4aα,4b,5,6,7,8,8aα,9,10,10aβdodecahydro-7β-hydroxy-4bβ-methyl-$\Delta^{2(1H)}$,$^\alpha$-phenanthreneacetate 7-acetate

[I; R is $CH_2CH_2N(CH_3)_2$, R° is H, R' is $CH_3$, R'' is H, X is $H_2$, Z is (β-$CH_3COO$)CH] was prepared by treating the 7β-hydroxy compound (Example 97) with an excess of acetic anhydride in pyridine, and was obtained in the form of its hydrochloride salt, m.p. 185.0°–189.0° C. when recrystallized from ethyl acetate.

By replacing the acetic anhydride in the previous example by caproyl chloride, β-cyclohexylpropionyl chloride, p-nitrobenzoyl chloride, cinnamoyl chloride or nicotinoyl chloride, there can be obtained, respectively, the 7-caproate, 7-(β-cyclohexylpropionate), 7-(p-nitrobenzoate), 7-cinnamate or 7-nicotinate of 2-dimethylaminoethyl 3,4,4aα,4b,5,6,7,8,8aα,9,10,-10aβ-dodecahydro-7β-hydroxy-4bβ-methyl-$\Delta^{2(1H)},\alpha$-phenanthreneacetate.

EXAMPLE 101

2-Dimethylaminoethyl
3,4,4aα,4b,5,6,7,8,8aα,9,10,10aβdodecahydro-3β-
hydroxy-4bβ-methyl-Δ$^{2(1H)}$,α-phenanthreneacetate
3-nitrate

[I; R is CH$_2$CH$_2$N(CH$_3$)$_2$, R° is H, R' is CH$_3$, R" is H, X is H$_2$, Z is (β-O$_2$NO)CH].

Ninety percent nitric acid (8ml.) was added slowly with stirring at −10° to 0° C. to 50 ml. of acetic anhydride. A solution of 4.00 g. (0.0115 moles) of the free base, 2-diethylaminoethyl 3,4,4aα,4b,5,6,7,8-,8aα,9,10,10aβ-dodecahydro-7β-hydroxy-4bβ-methyl-Δ$^{2(1H)}$,α-phenanthreneacetate (Example 97), in 15 ml. of chloroform was then added dropwise with stirring at −5° to −10° C. over a quarter-hour period. This solution was kept cold for 90 minutes and then poured into 400 ml. of ice and water. The mixture was allowed to stand for one hour, made alkaline with concentrated ammonium hydroxide and extracted twice with ether. The extracts were washed with brine and concentrated to a residue by warming under reduced pressure. The oily residue was chromatographed on silica gel-coated plates which were developed with 1:1:98 methanol-iopropylamine-chloroform. The loading amounted to about 0.4 g. per 20 × 40 cm. plate carrying a 1-mm. coating of silica gel. The principal band from the plates afforded an oil whose infrared spectrum showed no hydroxyl absorption. The oil was desolvated under reduced pressure at 54° C., dissolved in 10 ml. of ether and treated with 2.0 ml. of 6N alcoholic hydrogen chloride. The precipitated solid was boiled with 15 ml. of acetone and the mixture was cooled and filtered. The crystalline salt was then recrystallized by diluting a solution of it in 15 ml. of warm methanol with ether to the point of cloudiness. This mixture was diluted with 100 ml. of ether and filtered to give 2-dimethylaminoethyl 3,4,4aα,4b,5,6,7,8,8aα,9,10,10aβ-dodecahydro-3β-hydroxy-4bβ-methyl-Δ$^{2(1H)}$,α-phenanthreneacetate 3-nitrate in the form of its hydrochloride salt, colorless plates, m.p. 180°–181° C. (dec.).

EXAMPLE 102 a. 2-(Carbobenzoxyamino)-ethyl
3,4,4aα,4b,5,6,7,8,8aα,9,10,10aβ-dodecahydro-4bβ-
methyl-7-oxo-Δ$^{2(1H)}$,α-phenanthreneacetate.

A solution of 4,84 g. (0.0175 mole) of 3,4,4aα,4b,5,6,-7,8,8aα,9,10,10aβ-dodecahydro-4bβ-methyl-7-oxo-Δ$^{2(1H)}$,α-phenanthreneacetic acid (Example 61) in 30 ml. of dimethylsulfoxide was treated with 0.99 g. (0.018 mole) of sodium methoxide followed by 4.74 g. (0.0183 mole) of benzyl 2-bromoethylcarbamate. This mixture was allowed to stand for 75 minutes at room temperature, heated at 100° C. for 4 ¼ hours, cooled, diluted with 150 ml. of water and extracted twice with ether. Concentration of the extracts gave an oil (8g.) which was chromatographed on twenty-two 20 × 40 cm. silica chromatoplates developed with 1:4 ethyl acetate-chloroform. Thee 6.13 g. of oil (77%) was cleaved with trifluoroacetic acid as described below.

By replacing the benzyl 2-bromoethylcarbamate in the foregoing preparation by a molar equivalent amount of benzyl N-methyl-2-bromoethylcarbamate or benzyl N-(1-piperazinyl)-2-bromoethylcarbamate there can be obtained, respectively, 2-'carbobenzoxy-(N-methyl)amino]-ethyl 3,4,4aα,4b,5,6,7,8,8aα,-9,10,10aβ-dodecahydro-4bβ-methyl-7-oxo-Δ$^{2(1H)}$,α-phenanthreneacetate or 2-[carbobenzoxy-(N-1-piperazinyl)-amino]-ethyl 3,4,4aα,4b,5,6,7,8-,8aα,9,10,10aβ-dodecahydro-4bβ-methyl-7-oxo-Δ$^{2(1H)}$,α-phenanthreneacetate. b.

2-Aminoethyl
3,4,4aα,4b,5,6,7,8,8aα,9,10,10aβ-dodecahydro-
4bβ-methyl-7-oxo-Δ$^{2(1H)}$,α-phenanthreneacetate

[I; R is CH$_2$CH$_2$NH$_2$, R° is H, R' is CH$_3$, R" is H, X is H$_2$, Z is O=C].

A solution of 3.59 g. (0.0079 mole) of the carbobenzoxyamino ester, obtained in part (a) above, in 20 ml. of commercial trifluoroacetic acid was allowed to stand for 24 hours. The solution was diluted with 30 ml. of pentane, the mixture was stirred thoroughly and the supranatant liquid was decanted from an oily layer. This process was repeated four times. Then 5 ml. of ether was added, the mixture was stirred, 50 ml. of pentane was added and the supernatant liquid was decanted. This process was repeated twice. The oily product was then diluted with a few ml. of acetone and streaked on ten 20 cm. × 40 cm. silica plates which were developed with 3:3:94 methanol-isopropylamine-chloroform. The principal bands were quickly scraped off and eluted with 1:19 isopropylaminetetrahydrofuran (THF). The eluate was concentrated to a residue at <25° C. under reduced pressure, the flask was flushed free of isopropylamine with nitrogen and an additional 25 ml. of THF was added and evaporated to remove traces of isopropylamine. The residual oil was dissolved in 50 ml. of THF and an excess of gaseous hydrogen chloride was added. The amorphous precipitate was dissolved in 20 ml. of 95% ethanol and this solution was diluted with 10 ml. of acetone followed by 50 ml. of ether which was added in increments to allow the precipitate to crystallize. The slightly sticky solid was triturated with 10 ml. of acetone to give 2-aminoethyl 3,4,4aα,4b,5,6,7,8,8aα,9,10,10aβ-dodecahydro -4bβ-methyl-7-oxo-Δ$^{2(1H)}$,α-phenanthreneacetate in the form of its hydrochloride salt, m.p. 258°–259° C.

Similarly, 2-[carbobenzoxy-(N-methyl)amino]-ethyl 3,4,4aα,4b,5,6,7,8,8aα,9,10,10aβ-dodecahydro-4bβ-methyl-7-oxo-Δ$^{2(1H)}$,α-phenanthreneacetate or 2-[carbobenzoxy-(N-1-piperazinyl)-amino]-ethyl 3,4,4aα,4b,5,6,7,8,8aα,9,10,10aβ-dodecahydro-4bβ-methyl-7-oxo-Δ$^{2(1H)}$,α-phenanthreneacetate can be cleaved with trifluoroacetic acid to give, respectively, 2-methylaminoethyl 3,4,4aα,4b,5,6,7,8,8aα,9,10,-10aβ-dodecahydro-4bβ-methyl-7-oxo-Δ$^{2(1H)}$,α - phenanthreneacetate [I; R is CH$_2$CH$_2$NHCH$_3$, R° is H, R' is CH$_3$, R" is H, X is H$_2$, Z is O=C]; or 2-(1-piperazinyl)ethyl 3,4,4aα,4b,5,6,7,8,8aα,9,10,10aβ-dodecahydro-4bβ-methyl-7-oxo-Δ$^{2(1H)}$,α-phenanthreneacetate [I; R is CH$_2$CH$_2$N(CH$_2$)$_4$NH, R° is H, R' is CH$_3$, R" is H, X is H$_2$, Z is O=C].

EXAMPLE 103

2-Dimethylaminoethyl
3,4,4aα,4b,5,6,7,8,8aα,9,10,10aβ-dodecahydro-4bβ-
methyl-7-oxo-Δ$^{2(1H)}$,α-phenanthreneacetate
amidinohydrazone

[I; R is CH$_2$CH$_2$N(CH$_3$)$_2$, R° is H, R' is CH$_3$, R" is H, X is H$_2$, Z is H$_2$NC(=NH)NHN=C].

A solution of 5.60 g. (0.0161 mole) of 2-dimethylaminoethyl 3,4,4aα,4b,5,6,7,8,8aα,9,10,10aβ-dodecahydro-4bβ-methyl-7-oxo-Δ$^{2(1H)}$,α-phenanthreneacetate (Example 81) and 1.2 ml. of concentrated hydrochloric acid in 25 ml. of methanol was added to 175 ml. of 1N methanolic hydrogen chloride in which has been dissolved 6.0 g. (0.044 mole) of aminoguanidine bicarbonate. The solution was allowed to stand at room temperature for 41 hours and was then treated with solid sodium bicarbonate until neutral. The solvents were removed by warming under reduced pressure and the residue was dissolved in 1:4 acetic acid-water. A small insoluble residue was removed by filtration and the filtrate was cooled in an ice bath while being made strongly alkaline with 35% aqueous sodium hydroxide. The precipitated product was collected and dried by addition and evaporation of several portions of ethyl acetate. The 6.8 g. residue was dissolved in 110 ml. of methanol and the solution was treated with 2.8 ml. of concentrated hydrochloric acid and 500 ml. of ether. This mixture was allowed to stand for 64 hours and was then filtered to give 5.45 g. of desired amidinohydrazone hydrochloride, m.p. 180°–200° C. It was recrystallized by dissolving it in ether and adding methanol to give a different polymorph of 2-dimethylaminoethyl 3,4,4a$\alpha$,4b,5,6,7,8,8a$\alpha$,9,10,10a$\beta$-dodecahydro-4b$\beta$-methyl-7-oxo-$\Delta^{2(1H)}$, $^\alpha$-phenanthreneacetate amidinohydrazone, m.p. 167° C.

EXAMPLE 104

N-(2-Dimethylaminoethyl) 3,4,4a$\alpha$,4b$\beta$,5,6,7,8,8a$\alpha$,9,10,10a$\beta$-dodecahydro-7-oxo-$\Delta^{2(1H)}$, $^\alpha$-phenanthreneacetamide.

The acid chloride of 3,4,4a$\alpha$,4b$\beta$,5,6,7,8,8a$\alpha$,9,10,10a$\beta$-dodecahydro-7-oxo-$\Delta^{2(1H)}$, $^\alpha$-phenanthreneacetic acid was prepared from 2.05 g. (7.8 mmoles) of the acid in the manner described above in Example 72. This acid chloride in 40 ml. of dry benzene was treated with 10 g. (114 mmoles) of N,N-dimethylethylenediamine and the mixture was heated on the steam bath for 5 minutes. Ether and saturated sodium bicarbonate were added and the layers were separated. The ether layer was extracted with six 100 ml. portions of 2N hydrochloric acid and the aqueous extracts were heated at 50° C. for 45 minutes to cleave any enamine present from reaction at C-7. This aqueous solutionn was made basic with 35% sodium hydroxide, the product was extracted with ether and the extracts were washed with brine, dried (Na$_2$SO$_4$) and concentrated. The resulting 1.8 g. of oil was purified by partition chromatography using 60 g. of infusorial earth. The principal band furnished 1.16 g. of colorless oil, which was converted to its methanesulfonate salt and recrystallized from acetone-ether to give N-(2-dimethylaminoethyl) 3,44a$\alpha$,4b$\beta$,5,6,7,8,8a$\alpha$,9,10,10a$\beta$-dodecahydro-7-oxo-$\Delta^{2(1H)}$, $^\alpha$-phenanthreneacetamide in the form of its methanesulfonate salt, colorless prisms, m.p. 140.0°–160.0° C.

N-(2-Dimethylaminoethyl) 3,4,4a$\alpha$,4b$\beta$,5,6,7,8,8a$\alpha$,9,10,10a$\beta$-dodecahydro-7-oxo-$\Delta^{2(1H)}$, $^\alpha$-phenanthreneacetamide caused a decrease in blood pressure, contractile force and heart rate when administered to dogs at an intravenous dose of up to 4 mg./kg.

EXAMPLE 105

2-Dimethylaminoethyl 3,4,4a$\alpha$,9,10,10a$\beta$-hexahydro-7-hydroxy-$\Delta^{2(1H),\alpha}$ - phenanthreneacetate

[II; R is CH$_2$CH$_2$N(CH$_3$)$_2$, R° and R''' are H] was prepared from 3,4,4a$\alpha$,4$\beta$,5,6,7,9,10,10a$\beta$-decahydro-4b$\beta$-hydroxy-7-oxo-$\Delta^{2(1H),\alpha}$ -phenanthreneacetic acid (Example 66) according to the procedure of Example 72, using partition chromatography on 60 g. of infusorial earth in the purification process. The product was obtained in the form of its hydrochloride salt, m.p. 203°–215° C. when recrystallized from acetone. During this reaction dehydration of the 4b$\beta$-hydroxy group and aromatization of Ring A occurred.

Normal esterification of 3,4,4a$\alpha$,4$\beta$,5,6,7,9,10,10a$\beta$-decahydro-4b$\beta$-hydroxy-7-oxo-$\Delta^{2(1H)}$, $^\alpha$-phenanthreneacetic acid can be effected by reacting the sodium salt of said acid with 2-diethylaminoethyl bromide to yield 2-diethylaminoethyl 3,4,4a$\alpha$,4b,5,6,7,9,10,10a$\beta$-decahydro-4b$\beta$-hydroxy-7-oxo-$\Delta^{2(1H)}$, $^\alpha$-phenanthreneacetate [I; R is CH$_2$CH$_2$N(CH$_3$)$_2$, R° is H, R' is OH, R'' is H, X is H$_2$, Z is O=C].

According to the procedure of Example 72, the following basic esters can be prepared from the corresponding acids:

2-Dimethylaminoethyl 3,4,4a$\alpha$,9,10,10a$\alpha$-hexahydro-7-methoxy-$\Delta^{2(1H)}$, $^\alpha$-phenanthreneacetate ]II; R is CH$_2$Ch$_2$N(CH$_3$)$_2$,R° is H, R''' is CH$_3$], 2-Dimethylaminoethyl 3,4,4a$\alpha$,4b$\beta$,5,6,7,8,8a$\alpha$,9,10,10a$\beta$-dodecahydro-7-methyl-7-hydroxy-$\Delta^{2(1H)}$, $^\alpha$-phenanthreneacetate [I; R is CH$_2$CH$_2$N(CH$_3$)$_2$, R° , R' and R'' are H, X is H$_2$, Z is (HO) (CH$_3$)C], 2Dimethylaminoethyl 3,4,4a$\alpha$,4b$\beta$,5,6,7,8,8,a$\alpha$,9,10,10a$\beta$-dodecahydro-7$\alpha$-methoxy-$\Delta^{2(1H)}$, $^\alpha$-phenanthreneacetate [I; R is CH$_2$CH$_2$N(CH$_3$)$_2$, R°, R' and R'' are H, X is H$_2$, Z is ($\alpha$-CH$_3$O)CH], 2-Dimethylaminoethyl 3,4,4a$\alpha$,4b$\beta$,5,6,7,8,8a$\alpha$,9,10,10a$\beta$-dodecahydro-7$\beta$-fluoro-$\Delta^{2(1H)}$, $^\alpha$-phenanthreneacetate [I; R is CH$_2$CH$_2$N(CH$_3$)$_2$, R°, R' and R'' are H, X is H$_2$, Z is ($\beta$-F)CH], 2-Dimethylaminoethyl 3,4,4a$\alpha$,4b$\beta$,5,6,7,8,8a$\alpha$,9,10,10a$\beta$-dodecahydro-7$\beta$-chloro-$\Delta^{2(1H)}$, $^\alpha$-phenanthreneacetate [I; R is CH$_2$CH$_2$N(CH$_3$)$_2$, R°, R' and R'' are H, X is H$_2$, Z is ($\beta$-Cl)CH], 2-Dimethylaminoethyl 3,4,4a$\alpha$,4b$\beta$,5,6,7,8,8a$\alpha$,9,10,10a$\beta$-dodecahydro-7$\beta$-bromo$\Delta^{2(1H)}$, $^\alpha$-phenanthreneacetate [I; R is CH$_2$CH$_2$N(CH$_3$)$_2$, R°, R' and R'' are H, X is H$_2$, Z is ($\beta$-Br)CH], 2-Dimethylaminoethyl 7,7-ethylenedioxy-3,4,4a$\alpha$,4b,5,6,7,8,8a$\alpha$,9,10,10a$\beta$-dodecahydro-4a$\beta$-methyl-$\Delta^{2(1H)}$, $^\alpha$-phenanthreneacetate [I; R is CH$_2$CH$_2$N(CH$_3$)$_2$, R° is H, R' is CH$_3$, R'' is H, X is H$_2$, Z is (ethylenedioxy)C], 2-Dimethylaminoethyl 7,7-(1,3-propylenedioxy)-3,4,4a$\alpha$,4b,5,6,7,8,8a$\alpha$,9,10,-10a$\beta$-dodecahydro-4b$\beta$-methyl-$\Delta^{2(1H)}$, $^\alpha$-phenanthreneacetate [I; R is CH$_2$CH$_2$N(CH$_3$)$_2$, R° is H, R' is CH$_3$, R'' is H, X is H$_2$, Z is (1,3-propylenedioxy)C], 2-Dimethylaminoethyl 7,7-(1,3-propylenedimercapto)-3,4,4a$\alpha$,4b,5,6,7,8,8a$\alpha$,9,10,10a$\beta$-dodecahydro-4b$\beta$-methyl-$\Delta^{2(1H)}$, $^\alpha$-phenanthreneacetate [I; R is CH$_2$CH$_2$N(CH$_3$)$_2$, R° is H, R' is CH$_3$, R'' is H, X is H$_2$, Z is (1,3-propylenedithio)C], 2-Dimethylaminoethyl 7,7-dibenzylmercapto-3,4,4a$\alpha$,4b,-5,6,7,8,8a$\alpha$,9,10,10a$\beta$-dodecahydro-4b$\beta$-methyl-$\Delta^{22(1H)}$, $^\alpha$-phenanthreneactate [I; R is CH$_2$CH$_2$N(CH$_3$)$_2$, R° is H, R' is CH$_3$, R'' is H, X is H$_2$, Z is (C$_6$H$_5$CH$_2$S)$_2$C], 2-Dimethylaminoethyl 3,4,4a$\alpha$,4b,5,6,7,8,8a$\alpha$,9,10,-10a$\beta$-dodecahydro-4b$\beta$-methyl-7$\beta$-diethylamino-$\Delta^{2(1H)}$, $^\alpha$-phenanthrene-acetate [I; R is CH$_2$CH$_2$N(CH$_3$)$_2$, R° is H, R' is CH$_3$, R'' is H, X is H$_2$, Z is [(C$_2$H$_5$)$_2$N]CH], 2-Dimethylaminoethyl 3,4,4aα,4b,5,6,7,8,8aα9,10,-10aβ-dodecahydro-4bβ-methyl-7β-piperidino-Δ$^{2(1H)}$, α-phenanthreneacetate [I; R is CH$_2$CH$_2$N(CH$_3$)$_2$, R° is H, R' is CH$_3$, R'' is H, X is H$_2$, Z is (CH$_2$)$_5$NCH], 2-Dimethylaminoethyl 8,8-dimethyl-7,10-dioxo-3,4,4aα,4bβ,5,6,7,8,10,10aβ-decahydro-Δ$^{2(1H)}$, α-phenanthreneacetate [I; R is CH$_2$CH$_2$N(CH$_3$)$_2$, R°, R'' and R'' are H, X is O, Z is O=C, 8,8-(CH$_3$)$_2$, Δ$^{8a,9}$], 2-Dimethylaminoethyl 3,4,4aα,4b,5,6,7,8,10,10aβ-decahydro-4bβ,8,8-trimethyl-7-oxo-Δ$^{2(1H)}$, α-phenanthreneacetate [I; R is CH$_2$CH$_2$N(CH$_3$)$_2$, R° is H, R'' is CH$_3$, R'' is H, X is H$_2$, Z is O=C, Δ$^{8a,9}$], 2-Dimethylaminoethyl 3,4,4aα,4bβ,5,6,7,8,10,10aβ-decahydro-7-oxo-10-hydroxy-Δ$^{2(1H)}$, α-phenanthreneacetate [I; R is CH$_2$CH$_2$N(CH$_3$)$_2$, R°, R' and R'' are H, X is (H)(OH), Z is O=C, Δ$^{8a,9}$], and 2-Dimethylaminoethyl 3,4,4aα,4bβ,5,6,7,8-,8aα,9,10,10aβ-dodecahydro-7β-(N-phenylcarbamoyloxy)-$^{2(1H)}$, α-phenanthreneacetate [I; R is CH$_2$CH$_2$N(CH$_3$)$_2$, R°, R' and R'' are H, X is H$_2$, Z is (β-C$_6$H$_5$NHCOO)CH].

EXAMPLE 106

Ethyl 3,4,4aα, 4b, 5,6,7,8,8aα, 9, 10,10aβ-dodecahydro-7β-(4-hydroxypiperidino)-4bβ-methyl-Δ$^{2(1H)}$, α-phenanthreneacetate

[I; R is C$_2$H$_5$, R° is H, R' is CH$_3$, R'' is H, X is H$_2$, Z is HOCH(CH$_2$CH$_2$)$_2$NCH] was prepared from ethyl 3,4,4aα,4b,5,6,7,8,8Aα,9,10,10aβ-dodecahydro-4bβ-methyl-7-oxo-Δ$^{2(1H)}$, α-phenanthreneacetate (Example 43) and 4-hydroxypiperidine followed by treatment with formic acid, according to the procedure of Example 70. The product was obtained in the form of its hydrochloride salt as a colorless crystalline powder, m.p. 198°–203° C.

Ethyl 3,4,4aα,4b,5,6,7,8,8aα,9,10,10aβ-dodecahydro-7β-(4-hydroxypiperidino)-4bβ-methyl-Δ$^{2(1H)}$, α-phenanthreneacetate can be hydrolyzed with aqueous sodium hydroxide according to the procedure of Example 52 to afford 3,4,4aα,4b,5,6,7,8,8aα,9,10,10aβ-dodecahydro-7β-(4-hydroxypiperidino)-4bβ-methyl-Δ$^{2(1H)}$, α-phenanthreneacetic acid, in which in turn can be converted to its acid chloride and reacted with 2-dimethylaminoethanol according to the procedure of Example 72 to give 2-diethylaminoethyl 3,4,4aα,4b,5,6,7,8,8aα,9,10,10aβ-dodecahydro-7β-(4-hydroxypiperidino)-4bβ-methyl-Δ$^{2(1H)}$, α-phenanthreneacetate.

EXAMPLE 107

Preparation of optically active forms of 2-dimethylaminoethyl trans-3,4,4aα,4bβ,5,6,7,8,8aα,9,10,10aβ-dodecahydro-7β-hydroxyΔ$^{2(1H)}$, α-phenanthraneacetate.

a. Ethyl dl-trans-3,4,4Aα,4bβ,5,6,7,8,8aα,9,10,10aβ-dodecahydro-7β-hydroxy-Δ$^{2(1H)}$, α-phenanthreneaacetate.

The crude mixture of cis and trans isomers of this compound (41 g.) prepared as described in Example 32 was dissolved in 100 ml. of cyclohexane and the solution cooled to give 16.5 g. of a 3:7 mixture of cis and trans isomers. A second recrystallization from cyclohexane furnished 15.2 g. of needles, m.p. 96°–114° C. Recrysttallization of this mixture from 150 ml, of ether concentrated to a 50 ml. volume afforded 7.35 g. of needles, m.p. 118°–126.5° C. Recrystallization from hexane three more times raised the melting point to 126°–128.5° C. This produce was shown by glpc to contain 93% of the trans isomer and 7% of the cis isomer.

b. dl-trans-3,4,4aα,4bβ,5,6,7,8,8aα,9,10,10aβ-Dodecahydro-7β-hydroxy-Δ$^{2(1H)}$, α-phenanthreneacetic acid.

A solution of 5.7 g. (0.019 mole) of the 93% pure dl-trans ester described immediately above in 100 ml. of hot methanol was treated with 50 ml. of 2N sodium hydroxide solution and the mixture was refluxed for 1 hr. The methanol was removed by warming in vacuo and 200 ml. of water and 100 ml. of ether were added. This mixture was shaken thoroughly and then filtered to separate a considerable quantity of undissolved sodium salt of the product. The water layer from the filtrate was combined with the solid and the suspension was made strongly acidic with 2N hydrochloric acid. The precipitated acid was collected and air-dried; 5.7 g. Recrystallization of this product twice from acetonitrile afforded 3.7 g. (74%) of dl -trans acid, m.p. 221°–224° C. (evac. cap.). A third recrystallization of a portion of the product gave a sample as fine, colorless needles of m.p. 225°–227° C. (evac. cap.). Glpc on the methyl ester derivative, prepared with diazomethane, showed it to contain 1.6% of the cis isomer.

c. Resolution of dl-trans-3,4,4aα,4bβ,5,6,7,8,8aα,9,10,10aβ-dodecahydro-7β-hydroxy-Δ$^{2(1H)}$,α -phenanthreneacetic acid.

A solution of 3.70 g. of the dl-trans acid described immediately above in 50 ml. of hot methanol was treated with a solution of 4.00 g. of dehydroabietylamine in 10 ml. of hot methanol. A crystalline salt precipitated immediately. The mixture was cooled and filtered to give 5.19 g. of solid. The filtrate will be referred to below as the original filtrate.

Recrystallization of the 5.19 g. of solid twice from absolute ethanol with cooling only to room temperature produced 2.83 g. of needles of l-trans acid dehydroabietylamine salt, m.p. 232°–234° C. dec. (evac. cap.). A third recrystallization gave 2.40 g. of this salt which decomposed at 232.5°–234.5° C. (evac. cap.); [α]$_{D/25}$ = −19.7° (1% in HOAc).

The mother liquor from the recrystallization of the 5.19 g. of solid was concentrated to half its volume and 0.47 g. of needles was obtained showing [α]$_{D/25}$ = −3° (1% in HOAc). Concentration of the filtrate to dryness yielded 1.27 g. of solid, [α]$_{D/25}$ = +36° (1% in HOAc). This dextrorotatory residue was combined with the residue from the original filtrate and shaken with 85 ml. of water, 15 ml. of 2N sodium hydroxide and 100 ml. of ether. The ether layer was separated and washed with two 15 ml. portions of water. Acidification of the combined water layer and washings gave a crystalline precipitate which was washed well with water and air-dried; 1.57 g., [α]$_{D/25}$ = +40,3° (1% in EtOH). Multiple recrystallization of this enriched d-trans acid from acetonitrile failed to raise the melting point above 212°–216° C.; [α]$_{D/25}$ = +43.0° (1% in EtOH). Isolation of pure d-trans acid from this mixture is described later in this procedure.

The l-trans acid-dehydroabietylamine salt described earlier in this procedure (2.25 g.) was shaken with 85 ml. of water, 15 ml. of 2N sodium hydroxide solution and 100 ml. of ether and the layers were separated. The ether layer was washed with water and the combined aqueous layers were acidified with 2N hydrochloric acid. The precipitated l-trans acid was collected, washed with water and dried; 1.03 g.

A sample of the l-trans acid just described (0.87 g.) was converted to its l-1-(1-naphthyl)-ethylamine salt by dissolving it in 25 ml. of hot methanol and adding a solution of 0.57 g. of the l-amine in 10 ml. of methanol. Concentration of the resulting solution in vacuo to a 5 ml. volume, dilution with 35 ml. of ether and filtration gave 1.31 g. (91%) of l-trans acid l1-(1-naphthyl)ethylamine salt, m.p. 229°–231° C. with intumescence (evac. tube). Recrystallization from 110 ml. of methanol (with concentration to a 25 ml. volume) gave 1.06 g. of colorless plates and prisms, m.p. 231°–233.5° C. with intumescence, $[\alpha]_{D/25} = -27.5°$ (1% in HOAc).

Treatment of 0.96 g. of the 1-acid-1-base salt with base in the usual manner followed by acidification of the aqueous solution gave a crystalline acid which was recrystallized from 100 ml. of acetonitrile with concentration to a 35 ml. volume. Colorless needles of l-trans acid were obtained, m.p. 219°–220° C. (evac. tube); $[\alpha]_{D/25} = -49.4°$ (1% in EtOH).

Returning to the 1.57 g. of enriched d-trans acid (1.57 g., m.p. 212°–216° C.), a solution of this sample in 50 ml. of warm methanol was treated with a solution of 1.02 g. of d-1-(1-naphthyl)-ethylamine in 5 ml. of methanol. Cooling to 0° C. and filtration afforded 1.84 g. of colorless blades of the d-trans-acid-d-amine salt, m.p. 230°–231.5° C. with intumescence (evac. capillary); $[\alpha]_{D/25} = +29.2°$ (1% in HOAc). The filtrate was concentrated to a residue which was triturated twice with ether and then recrystallized from 25 ml. of methanol. Thus was obtained 0.22 g. of salt melting at 228.5–230° C. (intumescence) (evac. capillary). The combined crops were recrystallized from 150 ml. of methanol by concentrating the solution to a 60 ml. volume and cooling to 0° C. This process gave 1.54 g. of d-trans-acid-d-amine salt, blades, m.p. 230°–231° C. with intumescence (evac. capillary); $[\alpha]_{D/25} = +29.3°$.

d-trans-acid-d-amine d-trans-acid-d-amide salt (1.98 g.) was shaken with a mixture of 65 ml. of water 10 ml. of 2N sodium hydroxide and 50 ml. of ether and the layers were separated. The water layer was acidified with 2N hydrochloric acid and the precipitated d-trans-acid was washed with water and dried (1.17 g.). One recrystallization from acetonitrile gave 0.98 g. of colorless needles, m.p. 218°–220° C. (evac. capillary) and one further recrystallization raised the m.p. to its maximum at 219°–220° C. (evac. cap.); $[\alpha]_{D/25} = +49.0°$ (1% in EtOH).

d. 2Dimethylaminoethyl d-trans-3,4,4a$\alpha$,4b$\beta$,5,6,7,8,8,a$\alpha$,9,10,10a$\beta$-dodecahydro-7$\beta$-hydroxy-$\Delta^{2(1H),\alpha}$-phenanthreneacetate.

A solution of 0.90 g. of the d-trans acid in 10 ml. of methanol was treated with 3.40 ml. of 1N aqueous sodium hydroxide and the resulting solution was concentrated to a residue by warming in vacuo. This residue was dissolved in 15 ml. each of absolute ethanol and benzene, the solution was concentrated to a residue and the process was repeated. Then 25 ml. of benzene was added and distilled to give the sodium salt of the d-trans acid as a dry, colorless powder.

A stirred suspension of the sodium salt in 25 ml. of dry benzene and 0.20 ml. of pyridine was maintained at 10°–15° C. while 5.0 ml. of oxalyl chloride was added in 4 min. The mixture was stirred for 20 min. at the same temperature and was then concentrated to a residue at <30° C. in vacuo. The residue was suspended in 25 ml. of dry benzene and treated with 6.0 ml. of 2-dimethylaminoethanol dropwise with stirring at 10–15° C. in 3 min. Then the mixture was boiled for 15 min. with frequent stirring.

The reaction mixture was cooled and diluted with 10 ml. of water, 10 ml. of 2N ammonium hydroxide and 50 ml. of ether. The layers were separated and the aqueous layer was washed once with ether. The ether layers were combined, washed with brine and concentrated to a residual oil, which was chromatographed on six 20 × 40-cm. thick-layer silica gel plates using 3:3:94 methanol-isopropylamine-chloroform for development. The principal ultraviolet-absorbing band was scraped off and eluted with freshly distilled tetrahydrofuran. It was necessary to repeat the chromatographic process in order to remove a small quantity of less-polar impurity. Recrystallization of the 0.44 g. of crystalline product by dissolving it in 25 ml. of ether, filtering the solution through charcoal, concentrating to a 4 ml. volume and diluting with 20 ml. of pentane gave 0.36 g. of colorless needles, m.p. 112°–114° C. Recrystallization from ether and pentane in the same manner gave 0.27 g. of 2-dimethylaminoethyl d-trans-3,4,4a$\alpha$,4b$\beta$,5,6,7,8,8a$\alpha$,9,10,10a$\beta$-dodecahydro-7$\beta$-hydroxy-$\Delta^{2(1H),\alpha}$-phenanthreneacetate, melting at 113.5°–114.5° C. Recrystallization of this sample by dissolving it in 15 ml. of ether and concentrating the solution to a 1.5 ml. volume followed by cooling to −5° C. produced a different polymorphic form of the product as triangular plates. It underwent partial melting at 107°–108° C. with resolidification and finally melted at 115°–116° C. When the temperature of the m.p. bath was held at 102°–106° C. for five min., the sample failed to show the transitional melting and simply melted at the higher temperature. It showed $[\alpha]_D^{25} = +36.5°$.

e. 2-Dimethylaminoethyl l-tans-3,4,4a$\alpha$,4b$\beta$,5,6,7,8-,8a$\alpha$,9,10,10a$\beta$-dodecahydro-7$\beta$-hydroxy-$\Delta^{2(1H),\alpha}$-phenanthreneacetate was prepared from 1.90 g. of the l-trans acid in a manner identical with that described for the d-trans ester. The chromatographed product, 0.86 g., was recrystallized twice from ether and pentane as above to give 0.54 g. of colorless needles, m.p. 113.5°–114.5° C., $[\alpha]_D^{25} = -36.0°$.

The cardiotonic activities of the compounds of formulas I and II where R is amino-lower-alkyl were measured by standard methods in both the isolated appendage of the rabbit heart and in the intact dog. Cardiovascular activity in anesthetized, spontaneously respiring dogs was recorded on a polygraph. Heart contractile force was measured isometrically by means of a strain gauge arch sutured to the wall of the right ventricle. The test compounds in the form of their acid-addition salts were dissolved in distilled water and administered into the femoral vein at graduated dose levels ranging from 0.25 to 4 mg./kg. (calculated as the free base). The dose producing a 20% increase in contractile force ($ED_{20}$) was calculated from the dose-response curve. By the procedure the compounds of the invention were found to have $ED_{20}$ values ranging from 0.23 to 8 mg./kg.

We claim:

1. 1,2,3,4,4a,4b,5,6,7,8,10,10a-dodecahydro-7-oxo-phenanthrene bearing two lower-alkyl groups in the 8-position, a hydroxy or oxo group in the 2-position, and wherein the 10-position is unsubstituted or bears a hydroxy or acyloxy group wherein the acyl group is a carboxylic acyl group having from one to twelve carbon atoms and a molecular weight less than about 250.

2. 8,8-Di-lower-alkyl-1,2,3,4,4a,4b,5,6,7,8,10,10a-dodecahydro-7-oxo-2-phenanthrol, according to claim 1, wherein there is a hydroxy group in the 2-position and the 10-position is unsubstituted.

3. 3,4,4a,4b,5,6,7,8,10,10a-Decahydro-8,8-di-lower-alkyl-7-oxo-2(1H)-phenanthrone, according to claim 1, wherein there is an oxo group in the 2-position and the 10-position is unsubstituted.

4. 10-Acetoxy-8,8-di-lower-alkyl-3,4,4a,4b,5,6,7,8,10,10a-decahydro-7-oxo-2(1H)-phenanthrene, according to claim 1, wherein there is an oxo group in the 2-position and an acetoxy group in the 10-position.

5. 10-Acetoxy-8,8-di-lower-alkyl-1,2,3,4,4a,4b,5,6,7,8,10,10a-dodecahydro-2-phenanthrol, according to claim 1, wherein there is a hydroxy group in the 2-position and an acetoxy group in the 10-position.

* * * * *